US011644585B2

(12) United States Patent
Wu et al.

(10) Patent No.: US 11,644,585 B2
(45) Date of Patent: May 9, 2023

(54) SYSTEMS FOR IMAGING

(71) Applicant: SHANGHAI UNITED IMAGING HEALTHCARE CO., LTD., Shanghai (CN)

(72) Inventors: Guanghe Wu, Shanghai (CN); Fangjie Xu, Shanghai (CN); Kai Shao, Shanghai (CN); Huaifang Jiang, Shanghai (CN); Miao Li, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

(21) Appl. No.: 17/207,732

(22) Filed: Mar. 21, 2021

(65) Prior Publication Data

US 2021/0208294 A1    Jul. 8, 2021

Related U.S. Application Data

(63) Continuation of application No. PCT/CN2019/107084, filed on Sep. 20, 2019.

(30) Foreign Application Priority Data

Sep. 21, 2018  (CN) .......................... 201811107649.8
Jan. 30, 2019  (CN) .......................... 201910091503.7

(51) Int. Cl.
*G01T 1/29*    (2006.01)
*G01T 1/202*   (2006.01)
(Continued)

(52) U.S. Cl.
CPC .............. *G01T 1/2985* (2013.01); *A61B 6/03* (2013.01); *G01T 1/202* (2013.01); *H04N 5/32* (2013.01)

(58) Field of Classification Search
CPC ......... A61B 6/03; G01T 1/202; G01T 1/2985; H04N 5/32
See application file for complete search history.

(56) References Cited

U.S. PATENT DOCUMENTS 5,499,281 A  *  3/1996  Weedon ............... G01N 23/046
                                                      378/19
6,289,980 B1 *  9/2001  Insalaco ................ F28F 9/0243
                                                      165/174
(Continued)

FOREIGN PATENT DOCUMENTS

CN       201074930 Y     6/2008
CN       105769230 A     7/2016
(Continued)

OTHER PUBLICATIONS

International Search Report in PCT/CN2019/107084 dated Dec. 20, 2019, 5 pages.
(Continued)

*Primary Examiner* — Blake C Riddick
(74) *Attorney, Agent, or Firm* — Metis IP LLC

(57) ABSTRACT

The present disclosure is related to a system. The system may include a gantry, a detector assembly including a plurality of detector modules arranged on the gantry, and/or a cooling assembly configured to cool the detector assemble. Each of the plurality of detector modules may include a crystal array configured to detect radiation rays, and a shielding component configured to shield the crystal array from an electromagnetic interference. The cooling assembly may include a plurality of cooling components. Each of the plurality of cooling components may be embedded in a corresponding detector module of the plurality of detector modules.

17 Claims, 21 Drawing Sheets

(51) Int. Cl.
*H04N 5/32* (2006.01)
*A61B 6/03* (2006.01)

(56) References Cited

U.S. PATENT DOCUMENTS

| | | | |
|---|---|---|---|
| 10,353,084 B1* | 7/2019 | Wagner | A61B 6/037 |
| 2005/0285046 A1 | 12/2005 | Iwanczyk et al. | |
| 2007/0188175 A1 | 8/2007 | Burdick, Jr. et al. | |
| 2007/0267734 A1 | 11/2007 | Zhao et al. | |
| 2008/0006773 A1 | 1/2008 | Rose et al. | |
| 2009/0206836 A1* | 8/2009 | Eberler | A61B 5/055 |
| | | | 250/363.04 |
| 2009/0257548 A1* | 10/2009 | Joshi | A61B 6/035 |
| | | | 378/4 |
| 2010/0188082 A1 | 7/2010 | Morich et al. | |
| 2012/0242339 A1 | 9/2012 | Rey et al. | |
| 2014/0264041 A1 | 9/2014 | Schulz et al. | |
| 2014/0318156 A1 | 10/2014 | Richardson et al. | |
| 2015/0119704 A1* | 4/2015 | Roth | A61B 6/4258 |
| | | | 600/425 |
| 2015/0319830 A1* | 11/2015 | Lacey | A61B 6/035 |
| | | | 378/19 |
| 2016/0381842 A1 | 12/2016 | Liukkonen | |
| 2017/0059720 A1* | 3/2017 | McBroom | G01T 1/2985 |
| 2017/0176607 A1* | 6/2017 | Liu | H01L 31/024 |
| 2017/0299675 A1 | 10/2017 | Rigla Perez et al. | |
| 2018/0059270 A1* | 3/2018 | Hefetz | G01T 1/244 |
| 2018/0074144 A1* | 3/2018 | Dezorayev | G01T 1/2985 |
| 2019/0094390 A1* | 3/2019 | Polf | G01T 1/161 |
| 2019/0331810 A1 | 10/2019 | Yan et al. | |

FOREIGN PATENT DOCUMENTS

| | | |
|---|---|---|
| CN | 205377538 U | 7/2016 |
| CN | 205491405 U | 8/2016 |
| CN | 205562822 U | 9/2016 |
| CN | 106901772 A | 6/2017 |
| CN | 108272465 A | 7/2018 |
| CN | 108420447 A | 8/2018 |
| CN | 109223019 A | 1/2019 |
| CN | 109480885 A | 3/2019 |
| CN | 109620276 A | 4/2019 |
| JP | H11201561 A | 7/1999 |
| JP | 5588262 B2 | 9/2014 |
| JP | 2017090275 A | 5/2017 |
| KR | 20110066287 A | 6/2011 |
| WO | 2010067631 A1 | 6/2010 |

OTHER PUBLICATIONS

Written Opinion in PCT/CN2019/107084 dated Dec. 20, 2019, 7 pages.
First Office Action in Chinese Application No. 201910091503.7 dated Jan. 2, 2020, 24 pages.
Second Office Action in Chinese Application No. 201910091503.7 dated Aug. 17, 2020, 30 pages.
First Office Action in Chinese Application No. 201811107649.8 dated Mar. 31, 2021, 13 pages.
Peter D.Oicott et al., Novel Electra-Optical Coupling Technique for Magnetic Resonance-Compatible Positron Emission Tomography Detectors, Molecular Imaging, 8(2):74-86, 2009.
Ma, Yuedong, Optimization of coplanar-grid CdZnTe detector and their development in an array of detectors, Engineering Science and Technology II of Full-text Database of Outstanding Master's Theses in China, 2012, 126 pages.

* cited by examiner

22211

SYSTEMS FOR IMAGING

CROSS-REFERENCE TO RELATED APPLICATIONS

This application is a continuation of International Application No. PCT/CN2019/107084 field on Sep. 20, 2019, which claims priority of Chinese Patent Application No. 201811107649.8, filed on Sep. 21, 2018, and Chinese Patent Application No. 201910091503.7, filed on Jan. 30, 2019, the contents of each of which are hereby incorporated by reference.

TECHNICAL FIELD

This disclosure generally relates to an imaging system, and more particularly, relates to a detector module and a cooling assembly for imaging devices.

BACKGROUND

Medical imaging devices, such as a positron emission tomography (PET) device, have been widely used in clinical examinations and medical diagnoses in recent years. In the PET device, a detector assembly (e.g., a plurality of detector modules) is mounted in a 360-degree arc around a subject to collect coincident events that occur from a radioactive tracer given to the subject. Gamma photons emitted from the subject can be converted into electrical signals by the detector assembly and then processed to generate an image of the subject. The detector assembly of the PET device is thermally sensitive, a signal gain of the detector assembly can be changed with temperature fluctuations of the detector assembly, and characteristics of the detector assembly can also be changed with temperature fluctuations of the detector assembly. Several kinds of cooling systems are developed for cooling the detector assembly of the PET device. However, a traditional water cooling system typically generates temperature gradients among the plurality of detector modules of the PET device, which may result in a degradation of image quality. A traditional air cooling system, with the use of an air compressor, can bring noises when cooling the PET device. In addition, the traditional air cooling system typically do not meet a temperature requirement of the detector assembly. Thus, it is desirable to provide a cooling assembly that may cool a detector assembly of an imaging device effectively without noises.

Furthermore, the PET device is usually combined with another imaging system to take advantages of both modalities of imaging devices. For example, a PET-magnetic resonance (MR) is a hybrid imaging technique that incorporates both MR (e.g., a soft tissue morphological imaging technique) and PET (e.g., a functional imaging technique). In a conventional PET-MR device, components of a PET device (e.g., one or more PET detector modules) and components of an MR device (e.g., an RF coil, a main magnet, a gradient magnet) may be integrated. For example, a PET detector module may be placed between an RF coil and a gradient magnet of the MR device. As the RF coil and the PET detector module in the PET-MR device often work simultaneously, an interference or coupling between the RF coil and the PET detector module may occur and reduce the performance of either or both of the RF coil and the PET detector module. Therefore, it is desirable to provide a detector module that may reduce or eliminate an electromagnetic interference on the detector module.

SUMMARY

According to an aspect of the present disclosure, a detector module for a device may include a crystal array, and a shielding component. The crystal array may include a plurality of crystal units. The shielding component may be configured to house the crystal array. The shielding component may include a cover and a connection component. The cover may include an accommodating region configured to accommodate the crystal array. The connection component may be configured to connect the detector module to the device. The connection component may be operably coupled to the crystal array and the cover.

In some embodiments, the shielding component may further include a Faraday cage.

In some embodiments, the Faraday cage may be coupled to or integrated in the cover of the shielding component.

In some embodiments, the cover may include a plurality of boards, and at least one of the plurality of boards is detachable.

In some embodiments, the plurality of boards may include a first board and a second board. At least one of the first board or the second board may have a U-shaped cross section.

In some embodiments, at least one side of the first board may be bent toward the crystal array or bent away from the crystal array to form a protruding part, and a corresponding side of the second board is abutted against the protruding part.

In some embodiments, each of the plurality of boards may include a shielding layer in contact with the connection component. The shielding layer may be configured to conduct an electrical current. Shielding layers of adjacent boards may be in contact with each other.

In some embodiments, each of the plurality of boards may further include a base layer, and the shielding layer of the each board is placed on an outer surface of the base layer.

In some embodiments, an inner surface of the base layer may include a plurality of convex portions, and the connection component may include a plurality of concave portions corresponding to the plurality of convex portions.

In some embodiments, an inner surface of the base layer may include a plurality of concave portions, and the connection component may include a plurality of convex portions corresponding to the plurality of concave portions.

In some embodiments, the base layer may be made of an insulation material.

In some embodiments, the shielding layer may be made of an electrically conductive material.

In some embodiments, the shielding layer may have a configuration of a mesh.

In some embodiments, the shielding layer may include a plurality of grooves. Each of the plurality of grooves may penetrate an inner surface and an outer surface of the shielding layer. The shielding layer may include a plurality of portions associated with the plurality of grooves. Each two adjacent portions of the plurality of portions may be connected or contacted with each other.

In some embodiments, the connection component may include a connection block and at least one connection ring. The at least one connection ring may be sleeved on the connection block.

In some embodiments, the connection block may be made of an insulation material.

In some embodiments, the at least one connection ring may be made of an electrically conductive material. The at least one connection ring may be connected or contacted with the shielding layer.

In some embodiments, the detector module may include a cooling component configured to cool the crystal array.

In some embodiments, at least a portion of the cooling component may be located inside the cover and operably coupled to the crystal array.

In some embodiments, the crystal array may be configured to detect a radiation ray.

In some embodiments, the shielding component may be configured to shield the crystal array from an electromagnetic interference.

In some embodiments, the detector module may be a positron emission tomography (PET) detector module.

According to another aspect of the present disclosure, an imaging system may include a gantry and a detector assembly including a plurality of detector modules arranged on the gantry. Each of the plurality of detector modules may include a crystal array, and a shielding component. The crystal array may include a plurality of crystal units. The shielding component may be configured to house the crystal array. The shielding component may include a cover and a connection component. The cover may include an accommodating region configured to accommodate the crystal array. The connection component may be configured to connect the each detector module to the gantry. The connection component may be operably coupled to the crystal array and the cover.

According to another aspect of the present disclosure, a cooling assembly for a device may include a separator, a plurality of delivering tubes, and a collector. The separator may include a separation main tube, at least one separation chamber, and a plurality of separation branch tubes. The separation main tube may be in fluid communication with the at least one separation chamber. The plurality of separation branch tubes may be in fluid communication with the at least one separation chamber. The plurality of delivering tubes may be configured to deliver a cooling medium. Each delivering tube of the plurality of delivering tubes may be in fluid communication with each separation branch tube of the plurality of separation branch tubes. The each delivering tube may be configured to deliver a portion of the cooling medium to a target portion of the device. The collector may include a collection main tube and a plurality of collection branch tubes. Each collection branch tube of the plurality of collection branch tubes may be in fluid communication with the each delivering tube of the plurality of delivering tubes.

In some embodiments, the at least one separation chamber may include at least two levels of separation chambers. The at least two levels of separation chambers may include one or more first-stage separation chambers and one or more last-stage separation chambers. Each of the one or more first-stage separation chambers may be in fluid communication with at least one of the one or more last-stage separation chambers.

In some embodiments, the separation main tube may be in fluid communication with the one or more first-stage separation chambers. The each separation branch tube may be in fluid communication with one of the one or more last-stage separation chambers.

In some embodiments, an upper-stage separation chamber of the at least one separation chamber may be configured to deliver a portion of the cooling medium into a lower-stage separation chamber of the at least one separation chamber, in response to an amount of the cooling medium in the upper-stage separation chamber exceeding a threshold.

In some embodiments, the one or more last-stage separation chambers may include a plurality of separation grooves. The each of the one or more first-stage separation chambers may be in fluid communication with two or more of the plurality of separation grooves.

In some embodiments, each separation groove of the plurality of separation grooves may be in fluid communication with at least one separation branch tube of the plurality of separation branch tubes or at least two separation branch tubes of the plurality of separation branch tubes.

In some embodiments, a cross section of the each separation groove may have a curved shape or a flat shape.

In some embodiments, the at least one separation chamber may include one or more intermediate-stage separation chambers between the one or more first-stage separation chambers and the one or more last-stage separation chambers. One of the one or more intermediate-stage separation chambers may be in fluid communication with at least one of the one or more first-stage separation chambers and at least one of the one or more last-stage separation chambers.

In some embodiments, the separator may include at least one splitter plate configured to separate the at least one separation chamber. Each of the at least one splitter plate may include a connection area configured to allow a fluid communication between adjacent separation chambers of the at least one separation chamber.

In some embodiments, the device may include a plurality of detector modules. The target portion may include at least one detector module of the plurality of detector modules.

In some embodiments, at least one of the separator or the collector may be operably coupled to the target portion of the device.

In some embodiments, the cooling assembly may include at least one sensor configured to detect a status of the cooling medium in the cooling assembly.

In some embodiments, the status of the cooling medium may include at least one of a temperature or a flow rate of the cooling medium.

In some embodiments, the at least one sensor may be operably coupled to at least one of the separator, one of the plurality of delivering tubes, the collector, or a cooling source.

In some embodiments, each of the at least one sensor may be operably coupled to the each delivering tube, and configured to detect a temperature or a flow rate of the cooling medium in the each delivering tube.

In some embodiments, the at least one sensor may be operably coupled to a cooling source configured to generate the cooling medium. The at least one sensor may be configured to facilitate a control of the temperature or flow rate of the cooling medium generated by the cooling source.

In some embodiments, the separation main tube may include a first switch or valve configured to control a flow of the cooling medium in the separation main tube.

In some embodiments, the collection main tube may include a second switch or valve configured to control a flow of the heat-laden cooling medium in the collection main tube.

In some embodiments, a structure of the separator may be the same as a structure of the collector.

In some embodiments, a structure of the separator may be different from a structure of the collector.

In some embodiments, the collector may further include at least one collection chamber in fluid communication with the collection main tube and the plurality of collection branch tubes.

In some embodiments, a connection between the each separation branch tube and the each delivering tube and a connection between the each delivering tube and the each collection branch tube may be disposed on a same side of the target portion of the device.

In some embodiments, a connection between the each separation branch tube and the each delivering tube and a connection between the each delivering tube and the each collection branch tube may be disposed on different sides of the target portion of the device.

In some embodiments, the separator and the collector may be disposed on a same side of the target portion of the device.

In some embodiments, the separator and the collector may be disposed on different sides of the target portion of the device.

In some embodiments, the separator or the collector may be disposed surrounding the target portion of the device.

In some embodiments, the separator may be configured to separate the cooling medium into the plurality of delivering tubes.

In some embodiments, the collector may be configured to collect heat-laden cooling medium from the target portion of the device.

In some embodiments, the plurality of detector modules may include a positron emission tomography (PET) detector module.

According to another aspect of the present disclosure, an imaging system may include a gantry, a detector assembly including a plurality of detector modules arranged on the gantry, and a cooling assembly configured to cool the detector assembly. The cooling assembly may include a separator, a plurality of delivering tubes, and a collector. The separator may include a separation main tube, at least one separation chamber, and a plurality of separation branch tubes. The separation main tube may be in fluid communication with the at least one separation chamber. The plurality of separation branch tubes may be in fluid communication with the at least one separation chamber. The plurality of delivering tubes may be configured to deliver a cooling medium. Each delivering tube of the plurality of delivering tubes may be in fluid communication with each separation branch tube of the plurality of separation branch tubes. The each delivering tube may be configured to deliver a portion of the cooling medium to a target portion of the imaging system. The collector may include a collection main tube and a plurality of collection branch tubes. Each collection branch tube of the plurality of collection branch tubes may be in fluid communication with the each delivering tube of the plurality of delivering tubes.

According to another aspect of the present disclosure, a system may include a gantry, a detector assembly including a plurality of detector modules arranged on the gantry, and a cooling assembly configured to cool the detector assembly. Each of the plurality of detector modules may include a crystal array configured to detect radiation rays, and a shielding component configured to shield the crystal array from an electromagnetic interference. The cooling assembly may include a plurality of cooling components. Each of the plurality of cooling components may be embedded in a corresponding detector module of the plurality of detector modules.

In some embodiments, the cooling assembly may further include a plurality of delivering tubes configured to deliver a cooling medium to the plurality of cooling components. At least one of the plurality of delivering tubes may be in fluid communication with the each of the plurality of cooling components.

In some embodiments, the each of the plurality of cooling components may include at least one delivering tube configured to deliver a portion of the cooling medium, and a supporting board configured to support the at least one delivering tube.

In some embodiments, the at least one delivering tube may be embedded in the supporting board.

In some embodiments, the shielding component may include a cover and a connection component. The cover may include an accommodating region configured to accommodate the crystal array. The connection component may be configured to connect the each detector module to the gantry. The connection component may be operably coupled to the crystal array and the cover.

In some embodiments, the shielding component may further include a Faraday cage.

In some embodiments, the Faraday cage may be coupled to or integrated in the cover of the shielding component.

In some embodiments, the cover may include a plurality of boards, and at least one of the plurality of boards is detachable.

In some embodiments, the plurality of boards may include a first board and a second board. At least one of the first board or the second board may have a U-shaped cross section.

In some embodiments, at least one side of the first board may be bent toward the crystal array or bent away from the crystal array to form a protruding part, and a corresponding side of the second board is abutted against the protruding part.

In some embodiments, each of the plurality of boards may include a shielding layer in contact with the connection component. The shielding layer may be configured to conduct an electrical current. Shielding layers of adjacent boards may be in contact with each other.

In some embodiments, each of the plurality of boards may further include a base layer, and the shielding layer of the each board is placed on an outer surface of the base layer.

In some embodiments, an inner surface of the base layer may include a plurality of convex portions, and the connection component may include a plurality of concave portions corresponding to the plurality of convex portions.

In some embodiments, an inner surface of the base layer may include a plurality of concave portions, and the connection component may include a plurality of convex portions corresponding to the plurality of concave portions.

In some embodiments, the base layer may be made of an insulation material.

In some embodiments, the shielding layer may be made of an electrically conductive material.

In some embodiments, the shielding layer may have a configuration of a mesh.

In some embodiments, the shielding layer may include a plurality of grooves. Each of the plurality of grooves may penetrate an inner surface and an outer surface of the shielding layer. The shielding layer may include a plurality of portions associated with the plurality of grooves. Each two adjacent portions of the plurality of portions may be connected or contacted with each other.

In some embodiments, the connection component may include a connection block and at least one connection ring. The at least one connection ring may be sleeved on the connection block.

In some embodiments, the connection block may be made of an insulation material.

In some embodiments, the at least one connection ring may be made of an electrically conductive material. The at least one connection ring may be connected or contacted with the shielding layer.

In some embodiments, the cooling assembly may include a separator, a plurality of delivering tubes, and a collector. The separator may include a separation main tube, at least one separation chamber, and a plurality of separation branch tubes. The separation main tube may be in fluid communication with the at least one separation chamber. The plurality of separation branch tubes may be in fluid communication with the at least one separation chamber. The plurality of delivering tubes may be configured to deliver a cooling medium. Each delivering tube of the plurality of delivering tubes may be in fluid communication with each separation branch tube of the plurality of separation branch tubes. The each delivering tube may be configured to deliver a portion of the cooling medium to a target portion of the system. The collector may include a collection main tube and a plurality of collection branch tubes. Each collection branch tube of the plurality of collection branch tubes may be in fluid communication with the each delivering tube of the plurality of delivering tubes.

In some embodiments, the at least one separation chamber may include at least two levels of separation chambers. The at least two levels of separation chambers may include one or more first-stage separation chambers and one or more last-stage separation chambers. Each of the one or more first-stage separation chambers may be in fluid communication with at least one of the one or more last-stage separation chambers.

In some embodiments, the separation main tube may be in fluid communication with the one or more first-stage separation chambers. The each separation branch tube may be in fluid communication with one of the one or more last-stage separation chambers.

In some embodiments, an upper-stage separation chamber of the at least one separation chamber may be configured to deliver a portion of the cooling medium into a lower-stage separation chamber of the at least one separation chamber, in response to an amount of the cooling medium in the upper-stage separation chamber exceeding a threshold.

In some embodiments, the one or more last-stage separation chambers may include a plurality of separation grooves. The each of the one or more first-stage separation chambers may be in fluid communication with two or more of the plurality of separation grooves.

In some embodiments, each separation groove of the plurality of separation grooves may be in fluid communication with at least one separation branch tube of the plurality of separation branch tubes or at least two separation branch tubes of the plurality of separation branch tubes.

In some embodiments, a cross section of the each separation groove may have a curved shape or a flat shape.

In some embodiments, the at least one separation chamber may include one or more intermediate-stage separation chambers between the one or more first-stage separation chambers and the one or more last-stage separation chambers. One of the one or more intermediate-stage separation chambers may be in fluid communication with at least one of the one or more first-stage separation chambers and at least one of the one or more last-stage separation chambers.

In some embodiments, the separator may include at least one splitter plate configured to separate the at least one separation chamber. Each of the at least one splitter plate may include a connection area configured to allow a fluid communication between adjacent separation chambers of the at least one separation chamber.

In some embodiments, the target portion may include at least one detector module of the plurality of detector modules.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
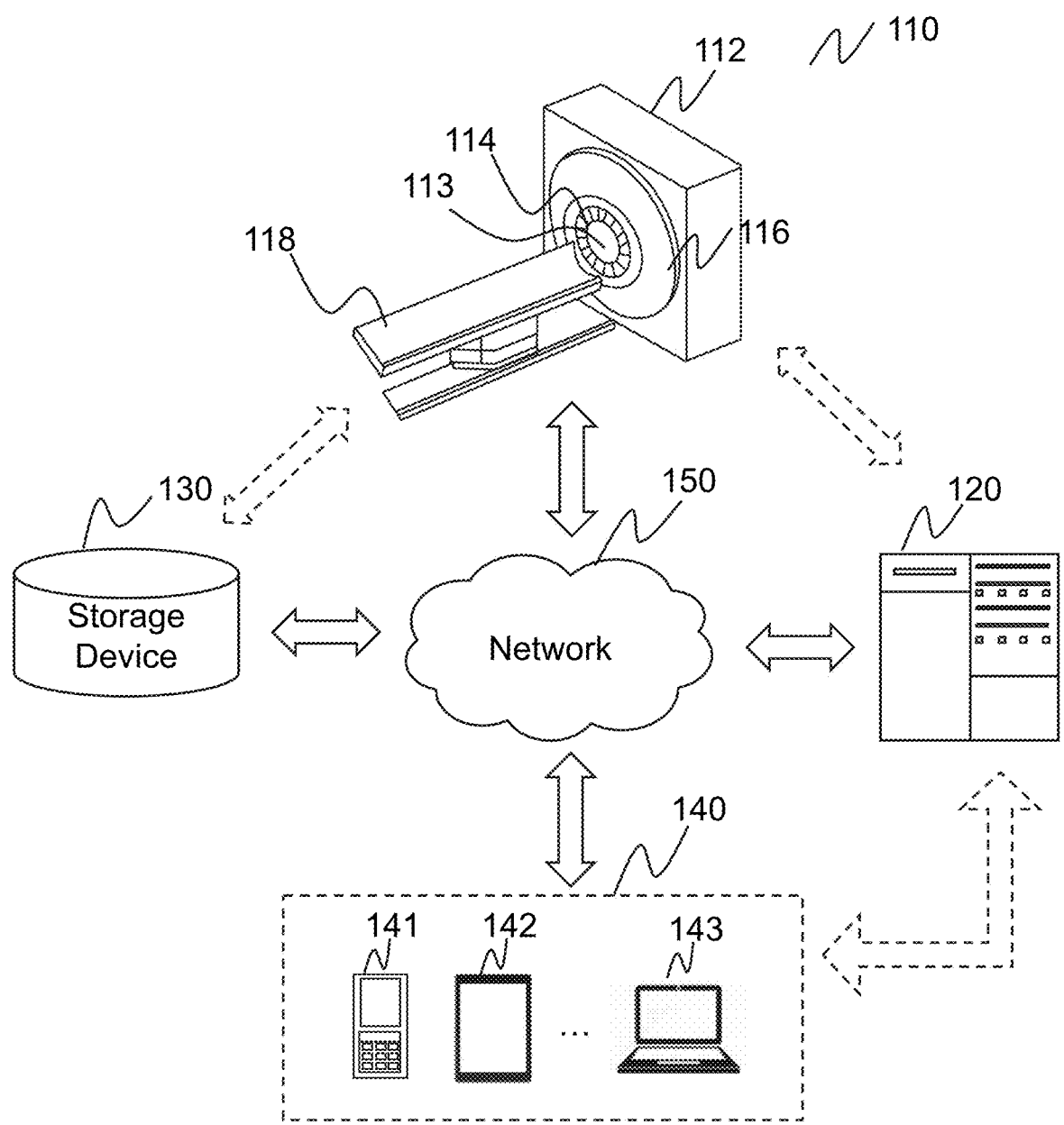
FIG. 1 is a schematic diagram illustrating an exemplary imaging system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. Also, the term "exemplary" is intended to refer to an example or illustration.

It will be understood that the terms "system," "engine," "unit," "module," and/or "block" used herein are one method to distinguish different components, elements, parts, sections or assembly of different levels in ascending order. However, the terms may be displaced by another expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that, although the terms "first," "second," "third," etc., may be used herein to describe various elements, these elements should not be limited by these terms. These terms are only used to distinguish one element from another. For example, a first element could be termed a second element, and, similarly, a second element could be termed a first element, without departing from the scope of exemplary embodiments of the present disclosure.

Spatial and functional relationships between elements are described using various terms, including "connected," "attached," and "mounted." Unless explicitly described as being "direct," when a relationship between first and second elements is described in the present disclosure, that relationship includes a direct relationship where no other intervening elements are present between the first and second elements, and also an indirect relationship where one or more intervening elements are present (either spatially or functionally) between the first and second elements. In contrast, when an element is referred to as being "directly" connected, attached, or positioned to another element, there are no intervening elements present. Other words used to describe the relationship between elements should be interpreted in a like fashion (e.g., "between," versus "directly between," "adjacent," versus "directly adjacent," etc.).

It should also be understood that terms such as "top," "bottom," "upper," "lower," "vertical," "lateral," "above," "below," "upward(s)," "downward(s)," "left-hand side," "right-hand side," "horizontal," and other such spatial reference terms are used in a relative sense to describe the positions or orientations of certain surfaces/parts/components of the imaging device with respect to other such features of the imaging device when the imaging device is in a normal operating position and may change if the position or orientation of the imaging device changes.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

For illustration purposes, the following description is provided to help better understanding a detector module and a cooling assembly. It is understood that this is not intended to limit the scope of the present disclosure. For persons having ordinary skills in the art, a certain amount of variations, changes and/or modifications may be deducted under the guidance of the present disclosure. Those variations, changes and/or modifications do not depart from the scope of the present disclosure.

An aspect of the present disclosure relates to a detector module for a device. The detector module (e.g., a PET detector module) may include a crystal array and a shielding component. The crystal array may include a plurality of crystal units. The shielding component may be configured to house the crystal array. The shielding component may include a cover and a connection component. The cover may include an accommodating region configured to accommodate the crystal array. The connection component may be configured to connect the detector module to the device (e.g., a PET device). The connection component may be operably coupled to the crystal array and the cover. In some embodiments, the shielding component may shield the crystal array from an electromagnetic interference. For example, in a PET-MR device, the shielding component may shield the PET detector module from at least part of an RF signal generated by an RF coil so as to reduce, e.g., an interference or coupling between the PET detector module and the RF coil. Furthermore, after a plurality of detector modules are assembled into a detector assembly, it is unnecessary to coat a copper foil on an outer surface of the detector assembly, and accordingly the assembly process of the detector assembly may be simplified.

Another aspect of the present disclosure relates to a cooling assembly for a device. The cooling assembly may include a separator, a plurality of delivering tubes, and a collector. The separator may include a separation main tube, at least one separation chamber, and a plurality of separation branch tubes. In some embodiments, the at least one separation chamber may include at least two levels of separation chambers (e.g., one or more first-stage separation chambers and one or more last-stage separation chambers). The separation main tube may be in fluid communication with the at least one separation chamber. The plurality of separation branch tubes may be in fluid communication with the at least one separation chamber. Each delivering tube of the plurality of delivering tubes may be in fluid communication with each separation branch tube of the plurality of separation branch tubes. The each delivering tube may be configured to deliver a portion of the cooling medium to a target portion of the device (e.g., a detector module). The collector may include a collection main tube and a plurality of collection branch tubes. Each collection branch tube of the plurality of collection branch tubes may be in fluid communication with the each delivering tube of the plurality of delivering tubes. The configuration of the at least two levels of separation chambers may ensure a uniform flow distribution of the cooling medium in the one or more last-stage separation chambers. Therefore, the cooling medium may be separated in the plurality of delivering tubes uniformly, and a circumferential flow gradient may be eliminated. Accordingly, temperature gradients among a plurality of detector modules in the device may also be eliminated, which may improve the imaging quality of the device.

Another aspect of the present disclosure relates to a system. The system may include a gantry, a detector assembly, and a cooling assembly. The detector assembly may include a plurality of detector modules arranged on the gantry. Each of the plurality of detector modules may include a crystal array and a shielding component. The crystal array may be configured to detect radiation rays. The shielding component may be configured to shield the crystal array from an electromagnetic interference. The cooling assembly may be configured to cool the detector assembly. In some embodiments, the cooling assembly may include a plurality of cooling components. Each of the plurality of cooling components may be embedded in a corresponding detector module of the plurality of detector modules. Accordingly, an electromagnetic interference on the crystal array may be reduced or eliminated by the shielding component, and the detector assembly may be cooled by the cooling assembly, which may improve the imaging quality of the system.

FIG. 1 is a schematic diagram illustrating an exemplary imaging system according to some embodiments of the present disclosure. As shown, the imaging system 100 may include an imaging device 110, a processing device 120, a storage device 130, one or more terminal(s) 140, and a network 150. In some embodiments, the imaging device 110, the processing device 120, the storage device 130, and/or the terminal(s) 140 may be connected to and/or communicate with each other via a wireless connection (e.g., the network 150), a wired connection, or a combination thereof. The imaging system 100 may include various types of connection between its components. For example, the imaging device 110 may be connected to the processing device 120 through the network 150, or connected to the processing device 120 directly as illustrated by the bidirectional dotted arrow connecting the imaging device 110 and the processing device 120 in FIG. 1. As another example, the storage device 130 may be connected to the processing device 120 through the network 150, as illustrated in FIG. 1, or connected to the processing device 120 directly. As still another example, the terminal(s) 140 may be connected to the processing device 120 through the network 150, or connected to the processing device 120 directly as illustrated by the bidirectional dotted arrow connecting the terminal(s) 140 and the processing device 120 in FIG. 1. As still another example, the terminal(s) 140 may be connected to the imaging device 110 through the network 150, as illustrated in FIG. 1, or connected to the imaging device 110 directly. As still another example, the storage device 130 may be connected to the imaging device 110 through the network 150, or connected to the imaging device 110 directly as illustrated by the bidirectional dotted arrow connecting the imaging device 110 and the storage device 130 in FIG. 1.

The imaging device 110 may be configured to image a subject and generate imaging data used to generate one or more images relating to the subject. In some embodiments, the imaging device 110 may transmit the imaging data to the processing device 120 or the terminal 140 for further processing (e.g., generating one or more images). In some embodiments, the imaging data and/or the one or more images associated with the subject may be stored in the storage device 130, the processing device 120, and/or the terminal 140.

In some embodiments, the imaging device 110 may be a PET device, a computed tomography (CT) device, an X-ray imaging device, a digital subtraction angiography (DSA) device, a dynamic spatial reconstruction (DSR) device, an X-ray microscopy device, an MR device, a multimodality device, or the like, or any combination thereof. Exemplary multi-modality devices may include a PET-CT device, a SPECT-MR device, a PET-MR device, or the like. The subject may be biological or non-biological. In some embodiments, the subject may include a patient, a man-made object, or the like. In some embodiments, the subject may include a specific portion, an organ, and/or tissue of a patient. For example, the subject may include head, brain, neck, body, shoulder, arm, thorax, cardiac, stomach, blood vessel, soft tissue, knee, feet, or the like, or any combination thereof. In the present disclosure, "object" and "subject" are used interchangeably.

In some embodiments, the imaging device 110 may include a gantry 112, a scanning area 113, a detector assembly 114, a cooling assembly 116, and a table 118. The gantry 112 may be configured to support one or more components of the imaging device 110, for example, the detector assembly 114, the cooling assembly 116, or the like. In some embodiments, an inner surface of the gantry 112 may form the scanning area 113 where the subject is positioned for imaging. The detector assembly 114 may be configured to detect signals, for example, attenuated radioactive rays (e.g., X rays), radiation events (e.g., gamma photons), or the like. In some embodiments, the detector assembly 114 may include a plurality of detector modules. The plurality of detector modules may be arranged in a suitable configuration, including but not limited to a ring (e.g., a detector ring), a rectangle, a triangle, or an array. More descriptions of the detector assembly 114 may be found elsewhere in the present disclosure (e.g., FIGS. 2-6, and descriptions thereof). The cooling assembly 116 may be configured to produce, transfer, deliver, or circulate a cooling medium to the imaging device 110 to absorb heat produced by the imaging device 110 (e.g., the detector assembly 114) during an imaging procedure. More descriptions of the cooling assembly 116 may be found elsewhere in the present disclosure (e.g., FIGS. 2, 7-22, and descriptions thereof). The table 118 may be configured to support and/or transport the subject (e.g., a patient) to be imaged.

The processing device 120 may process data and/or information obtained from the imaging device 110, the storage device 130, and/or the terminal(s) 140. For example, the processing device 120 may reconstruct an image based on the image data. In some embodiments, the processing device 120 may be a single server or a server group. The server group may be centralized or distributed. In some embodiments, the processing device 120 may be local or remote. For example, the processing device 120 may access information and/or data from the imaging device 110, the storage device 130, and/or the terminal(s) 140 via the network 150. As another example, the processing device 120 may be directly connected to the imaging device 110, the terminal(s) 140, and/or the storage device 130 to access information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or a combination thereof.

The storage device 130 may store data, instructions, and/or any other information. In some embodiments, the storage device 130 may store data obtained from the imaging device 110, the processing device 120, and/or the terminal(s) 140. In some embodiments, the storage device 130 may store data and/or instructions that the processing device 120 and/or the terminal 140 may execute or use to perform exemplary methods described in the present disclosure. In some embodiments, the storage device 130 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform as described elsewhere in the disclosure.

In some embodiments, the storage device 130 may be connected to the network 150 to communicate with one or more other components in the imaging system 100 (e.g., the processing device 120, the terminal(s) 140). One or more components in the imaging system 100 may access the data or instructions stored in the storage device 130 via the network 150.

The terminal(s) 140 may be connected to and/or communicate with the imaging device 110, the processing device 120, and/or the storage device 130. In some embodiments, the terminal 140 may include a mobile device 141, a tablet computer 142, a laptop computer 143, or the like, or any combination thereof. For example, the mobile device 141 may include a mobile phone, a personal digital assistant (PDA), a gaming device, a navigation device, a point of sale (POS) device, a laptop, a tablet computer, a desktop, or the like, or any combination thereof.

The network 150 may include any suitable network that can facilitate the exchange of information and/or data for the imaging system 100. In some embodiments, one or more components of the imaging system 100 (e.g., the imaging device 110, the processing device 120, the storage device 130, the terminal(s) 140, etc.) may communicate information and/or data with one or more other components of the imaging system 100 via the network 150. For example, the processing device 120 and/or the terminal 140 may obtain image data from the imaging device 110 via the network 150. As another example, the processing device 120 and/or the terminal 140 may obtain information stored in the storage device 130 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network (VPN), a satellite network, a telephone network, routers, hubs, witches, server computers, and/or any combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the imaging system 100 may be connected to the network 150 to exchange data and/or information.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. However, those variations and modifications do not depart the scope of the present disclosure. In some embodiments, the imaging device 100 may further include a radiation source. The radiation source may include a high voltage generator, a tube, and a collimator. The high voltage generator may be configured to generate a high-voltage and current for the tube. The tube may generate and/or emit radiation beams traveling toward a subject. The radiation may include a particle ray, a photon ray, or the like, or any combination thereof. In some embodiments, the radiation may include a plurality of radiation particles (e.g., neutrons, protons, electron, p-mesons, heavy ions), a plurality of radiation photons (e.g., X-ray, a y-ray, ultraviolet, laser), or the like, or any combination thereof. The collimator may be configured to adjust the irradiation region (i.e., radiation field) on the subject.

Figure 2:
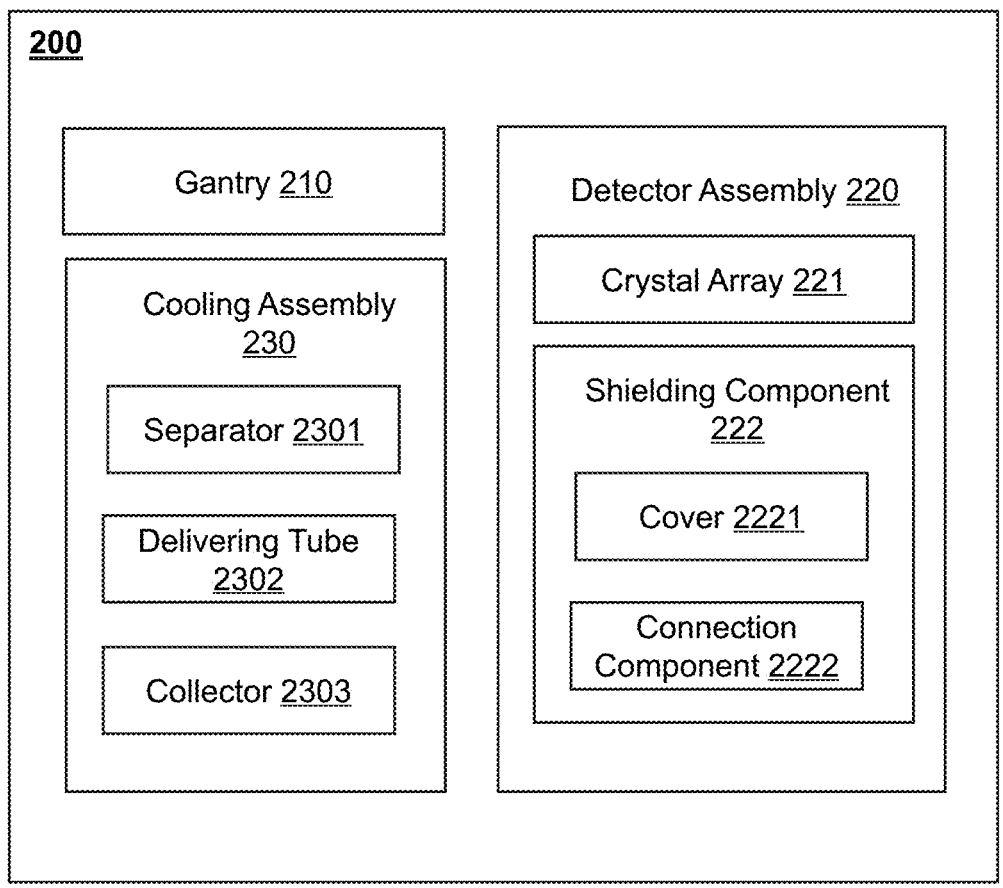
FIG. 2 is a schematic diagram illustrating an exemplary imaging device according to some embodiments of the present disclosure.

FIG. 2 is a schematic diagram illustrating an exemplary imaging device according to some embodiments of the present disclosure. In some embodiments, the imaging device 200 may be an example of the imaging device 110 or a portion of the imaging device 110. As shown in FIG. 2, the imaging device 200 may include a gantry 210, a detector assembly 220, and a cooling assembly 230. The detector assembly 220 may include a plurality of detector modules. Each detector module may include a crystal array 221 and a shielding component 222. The shielding component 222 may include a cover 2221 and a connection component 2222. The cooling assembly 230 may include a separator 2301, a plurality of delivering tubes 2302, and a collector 2303.

The gantry 210 may be configured to support one or more components (e.g., the detector assembly 220, the cooling assembly 230) of the imaging device 200. In some embodiments, an inner surface of the gantry 210 may form a scanning area (e.g., the scanning area 113). A subject to be scanned may be placed on a table (e.g., the table 118) and moved to a desired position in the scanning area and be imaged (e.g., undergoing an MR scan and/or a PET scan).

Figure 3:
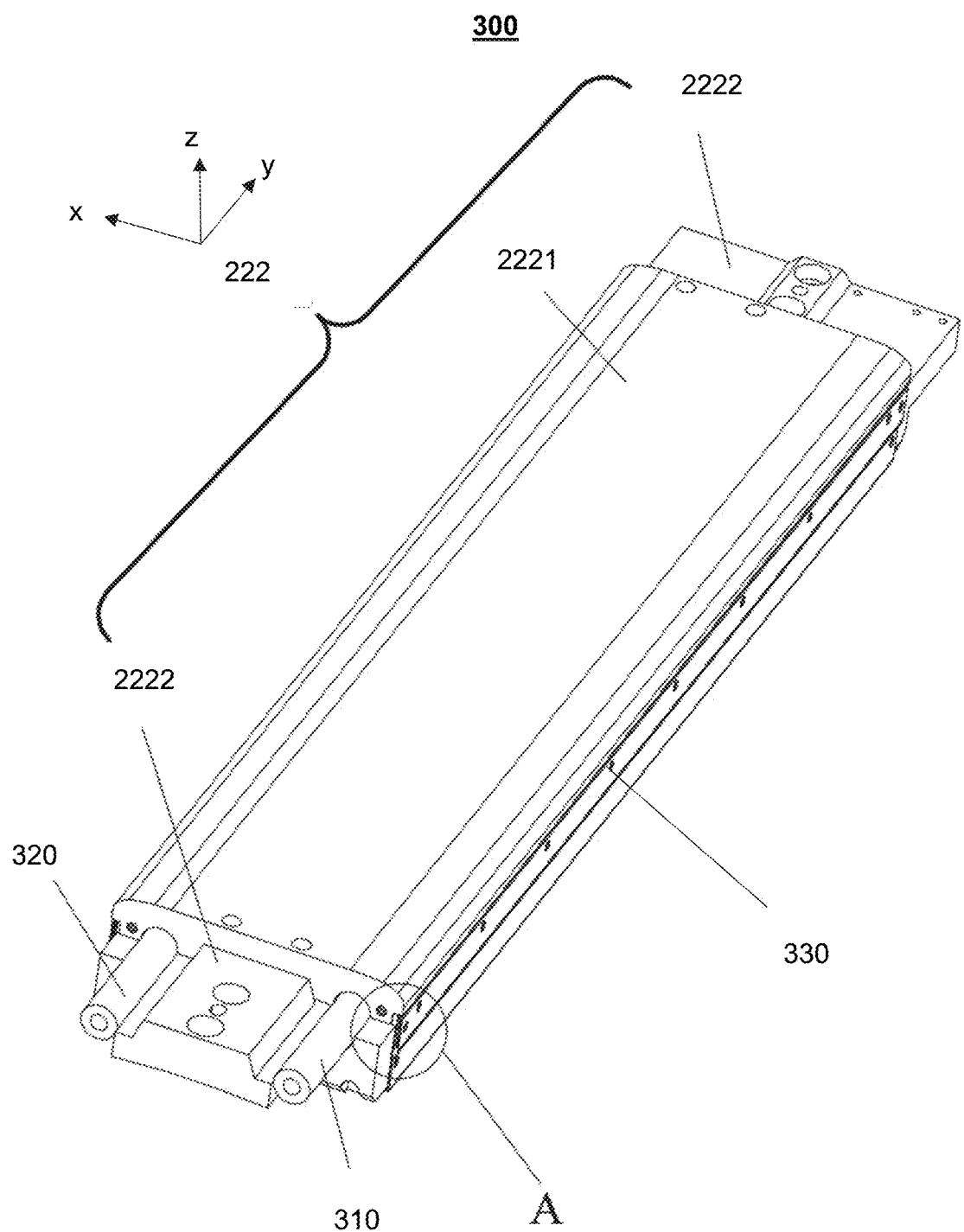
FIG. 3 is a schematic diagram illustrating an exemplary detector module according to some embodiments of the present disclosure.

The detector assembly 220 may be configured to detect signals associated with the subject, for example, attenuated radioactive rays, radiation events, or the like. For example, for a PET system, the detector assembly 220 may detect gamma photons. In some embodiments, the detector assembly 220 may include a plurality of detector modules (e.g., a detector module 300 as illustrated in FIG. 3). Each detector module may include a crystal array 221 and a shielding component 222.

Figure 5A:
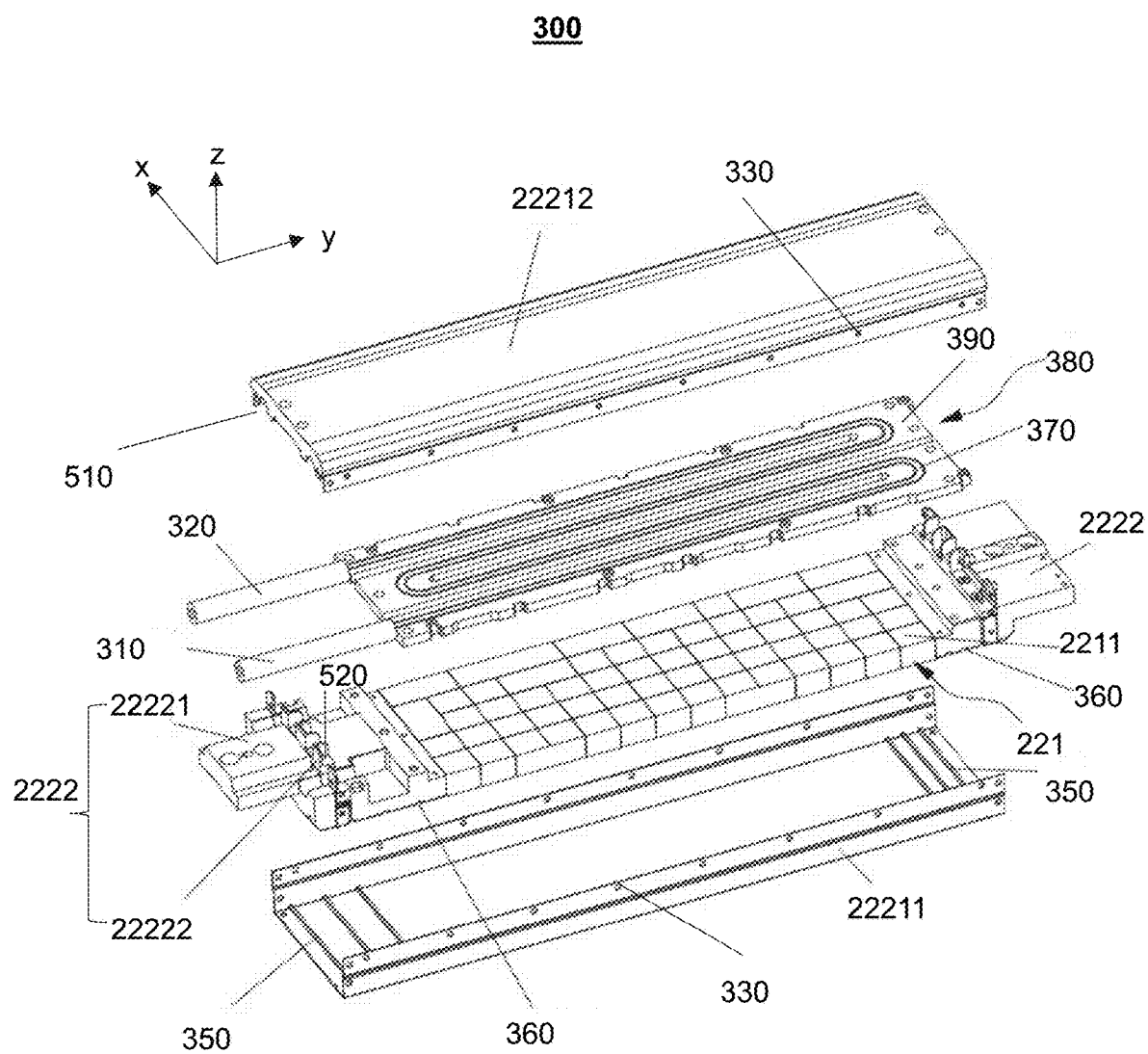
FIG. 5A is an exploded view of the exemplary detector module shown in FIG. 3 according to some embodiments of the present disclosure.

The crystal array 221 may be configured to detect radiation rays. In some embodiments, the crystal array 221 may include a plurality of crystal units (e.g., a plurality of crystal units 2211 as illustrated in FIG. 5A). In some embodiments, the crystal units may include scintillator crystals. The plurality of crystal units may be arranged in one or more rows and one or more columns. In some embodiments, the crystal array 221 may further include a plurality of photosensors (not shown) coupled to the plurality of crystal units and configured to convert a light signal (e.g., the light output from the scintillators) to an electrical signal. Exemplary photosensors may include a photomultiplier tube (PMT), a silicon photomultiplier (SiPM), etc.

The shielding component 222 may be configured to house the crystal array 221. In some embodiments, the shielding component 222 may include a cover 2221 and a connection component 2222. In some embodiments, the shielding component 222 may shield the crystal array 221 from an electromagnetic interference. For example, in a PET-MR device, the shielding component 222 may shield a PET detector module from at least part of RF signals generated by an RF coil so as to reduce, e.g., an interference or coupling between the PET detector module and the RF coil. In some embodiments, the shielding component 222 may include a Faraday cage. The Faraday cage may be coupled to or integrated in the cover 2221 of the shielding component 222. For example, the cover 2221 and the connection component 2222 may form a complete Faraday cage.

Figure 7:
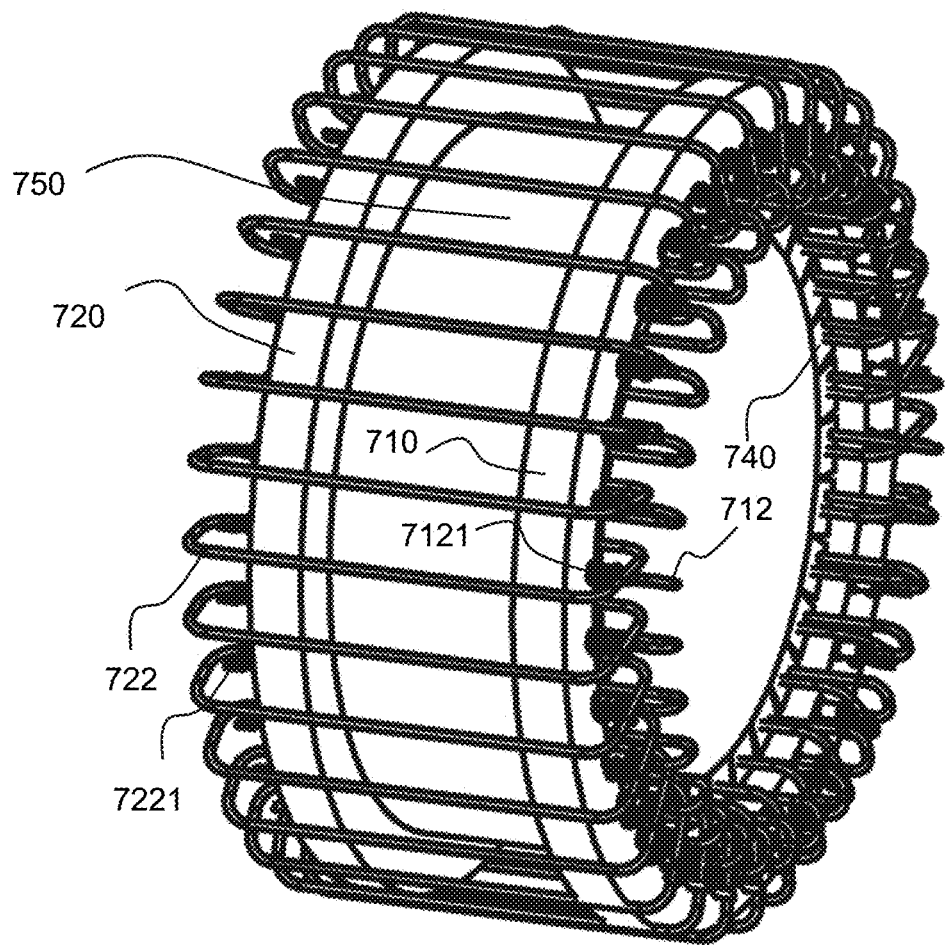
FIG. 7 is schematic diagram illustrating an exemplary cooling assembly according to some embodiments of the present disclosure.

The cover 2221 may include an accommodating region configured to accommodate the crystal array 221. In some embodiments, the cover 2221 may include a plurality of boards. At least one of the plurality of boards may be detachable. For example, the cover 2221 may include a first board and a second board as described elsewhere in the present disclosure (e.g., FIGS. 3-5, and descriptions thereof). The connection component 2222 may be configured to connect the detector module to the imaging device 200. The connection component 2222 may be operably coupled to the crystal array 221 and the cover 2221. For example, the detector module may be mounted on the gantry 210 via the connection component 2222. As another example, the detector module may be mounted on a supporting component (e.g., a supporting component 750 as illustrated in FIG. 7) of a cooling assembly 230 via the connection component 2222. In some embodiments, the connection component 2222 may include a connection block 22221 and at least one connection ring 22222 as described elsewhere in the present disclosure (e.g., FIGS. 3-5, and descriptions thereof).

The cooling assembly 230 may be configured to cool a target portion of the imaging device 200. The target portion may include one or more components (e.g., one or more detector modules in the detector assembly 220) of the imaging device 200. For example, a target portion may correspond to a detector module, and a plurality of target portions may need to be cooled. The cooling assembly 230 may cool the imaging device 200 such that temperatures of various target portions of the imaging device 200 are maintained at acceptable levels and the imaging device 200 functions properly. In some embodiments, the cooling assembly 230 may include the separator 2301, the plurality of delivering tubes 2302, and the collector 2303.

Figure 8:
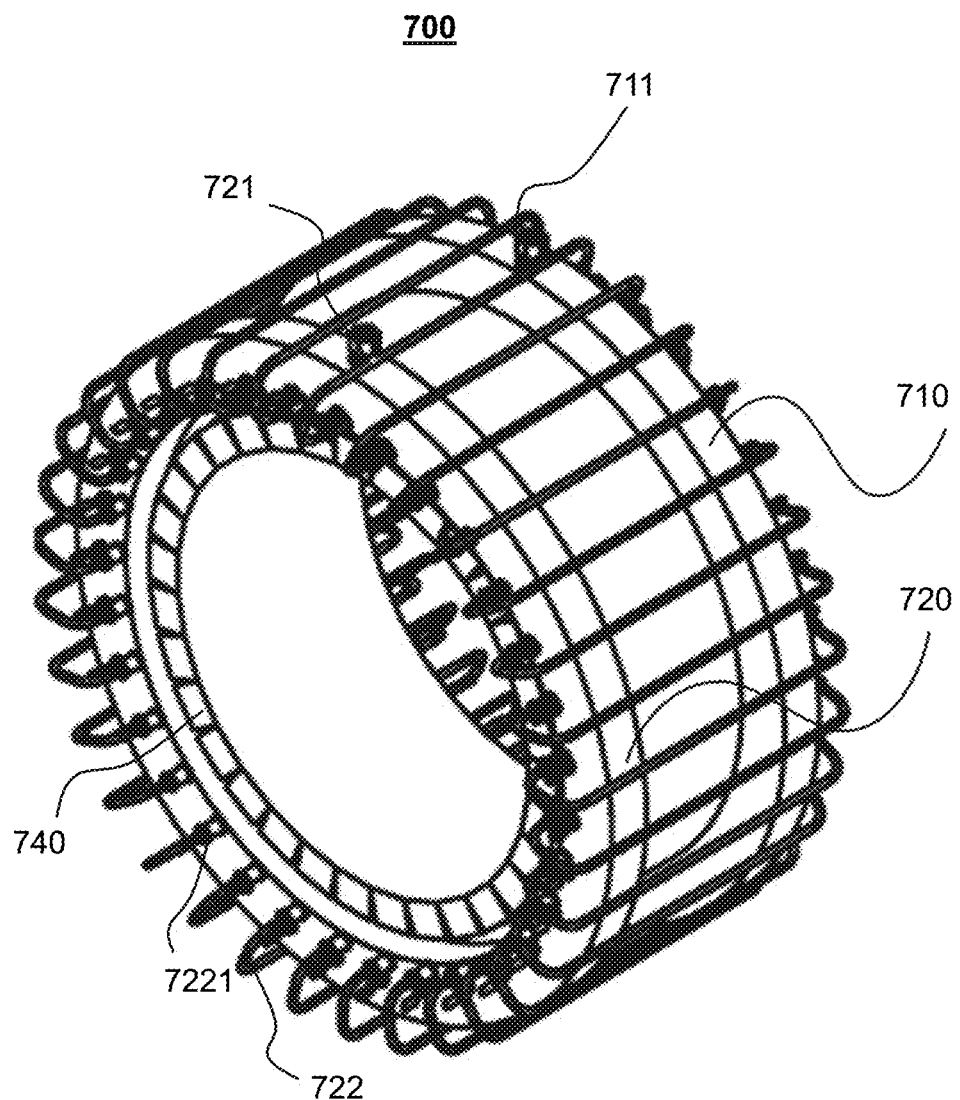
FIG. 8 is a schematic diagram illustrating an exemplary cooling assembly according to some embodiments of the present disclosure.
Figure 9:
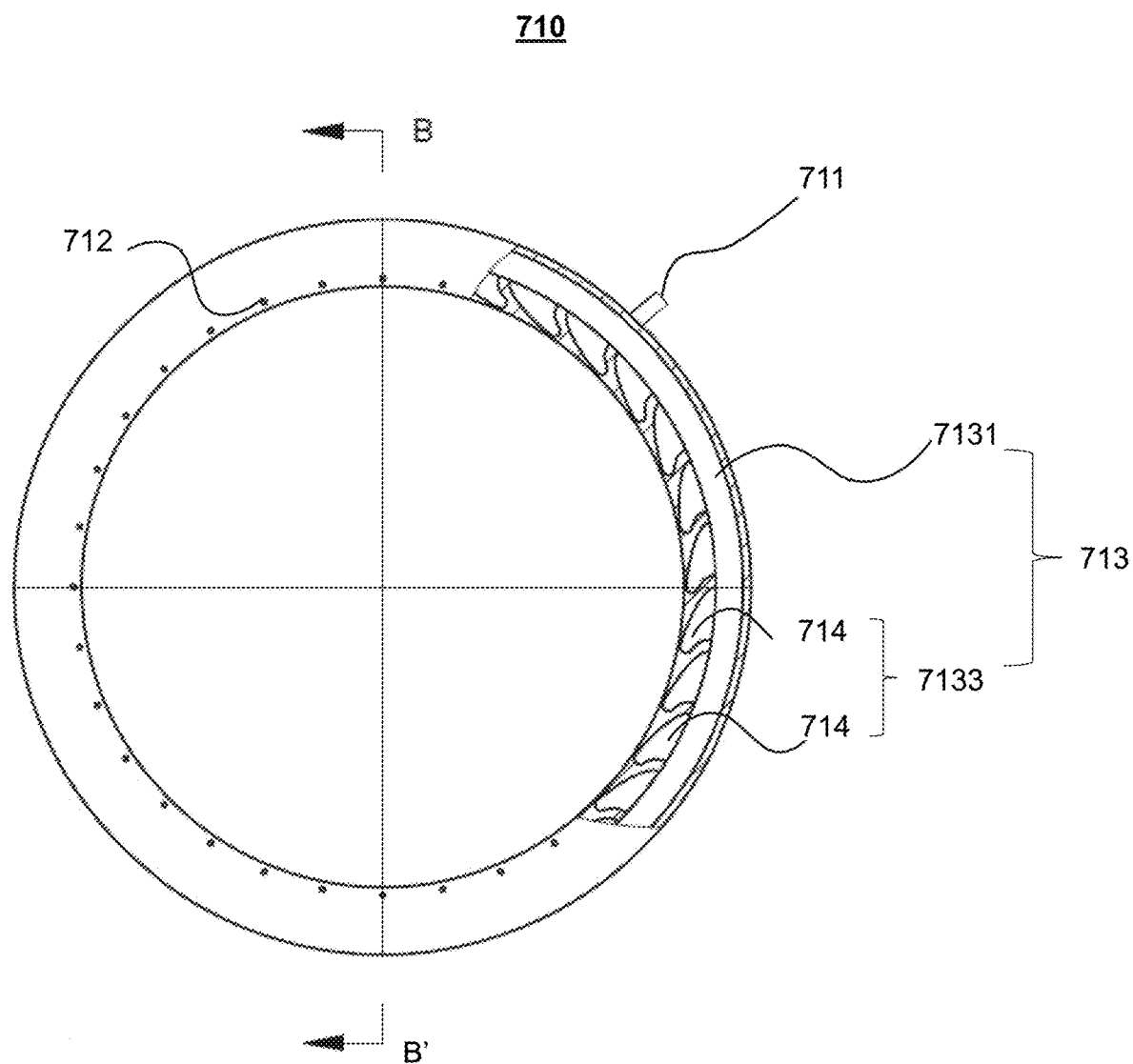
FIG. 9 is an axial sectional view of an exemplary separator according to some embodiments of the present disclosure.

The separator 2301 may be configured to separate a cooling medium into the plurality of delivering tubes 2302. The cooling medium may include a cooling gas (e.g., air), or a cooling liquid (e.g., water). In some embodiments, the separator 2301 may include a separation main tube (e.g., a separation main tube 711 as illustrated in FIG. 8), at least one separation chamber (e.g., a plurality of separation chambers 713 as illustrated in FIG. 9), and/or a plurality of separation branch tubes (e.g., a plurality of separation branch tubes 712 as illustrated in FIG. 7). The separation main tube may be in fluid communication with the at least one separation chamber. The plurality of separation branch tubes may be in fluid communication with the at least one separation chamber. More descriptions of the separator 2301 may be found elsewhere in the present disclosure (e.g., FIGS. 7-15, and descriptions thereof).

The delivering tube 2302 may be configured to deliver at least a portion of the cooling medium to a target portion of the imaging device 200. After the cooling medium absorbs heat from the target portion, a heat-laden cooling medium may be generated. In some embodiments, a number (or count) of the delivering tubes 2302 may be the same as a number (or count) of the detector modules in the detector assembly 220. For example, each delivering tube 2302 of the plurality of delivering tubes 2302 may correspond to a detector module of the plurality of detector modules (i.e., each delivering tube may be in fluid communication with a detector module). In some embodiments, the number (or count) of the delivering tubes 2302 may be different from the number (or count) of the detector modules in the detector assembly 220. For example, each delivering tube 2302 of the plurality of delivering tubes 2302 may correspond to two or more detector modules (i.e., each delivering tube may be in fluid communication with two or more detector modules). As another example, two or more delivering tubes 2302 may correspond to one detector module of the plurality of detector modules (i.e., two or more delivering tubes may be in fluid communication with a detector module). More descriptions of the delivering tube 2302 may be found elsewhere in the present disclosure (e.g., FIGS. 7-8, and descriptions thereof).

The collector 2303 may be configured to collect the heat-laden cooling medium from the target portion(s) of the imaging device 200. In some embodiments, the collector 2303 may include a collection main tube (e.g., a collection main tube 721 as illustrated in FIG. 8) and a plurality of collection branch tubes (e.g., a plurality of collection branch tubes 722 as illustrated in FIG. 7). Each collection branch tube of the plurality of collection branch tubes may be in fluid communication with at least one delivering tube 2302 of the plurality of delivering tubes 2302. In some embodiments, the collector 2303 may further include at least one collection chamber in fluid communication with the collection main tube and the plurality of collection branch tubes. More descriptions of the collector 2303 may be found elsewhere in the present disclosure (e.g., FIGS. 7-15, and descriptions thereof).

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the cooling assembly 230 may further include a supporting component (e.g., a supporting component 750 as illustrated in FIG. 7) configured to support the detector assembly 220 as described elsewhere in the present disclosure (e.g., FIGS. 7, 8, and descriptions thereof). In some embodiments, the cooling assembly 230 may further include at least one sensor configured to detect a status of the cooling medium in the cooling assembly 230 as described elsewhere in the present disclosure (e.g., FIGS. 7, 8 and descriptions thereof). In some embodiments, the cooling assembly 230 may include a plurality of cooling components (e.g., a cooling component 380 as illustrated in FIG. 5A). Each of the plurality of cooling components may be embedded in a corresponding detector module of the plurality of detector modules. In some embodiments, the detector module may include the cooling component (e.g., the cooling component 380 as illustrated in FIG. 5A) configured to cool the crystal array as described elsewhere in the present disclosure (e.g., FIG. 5A and descriptions thereof).

Figure 4A:
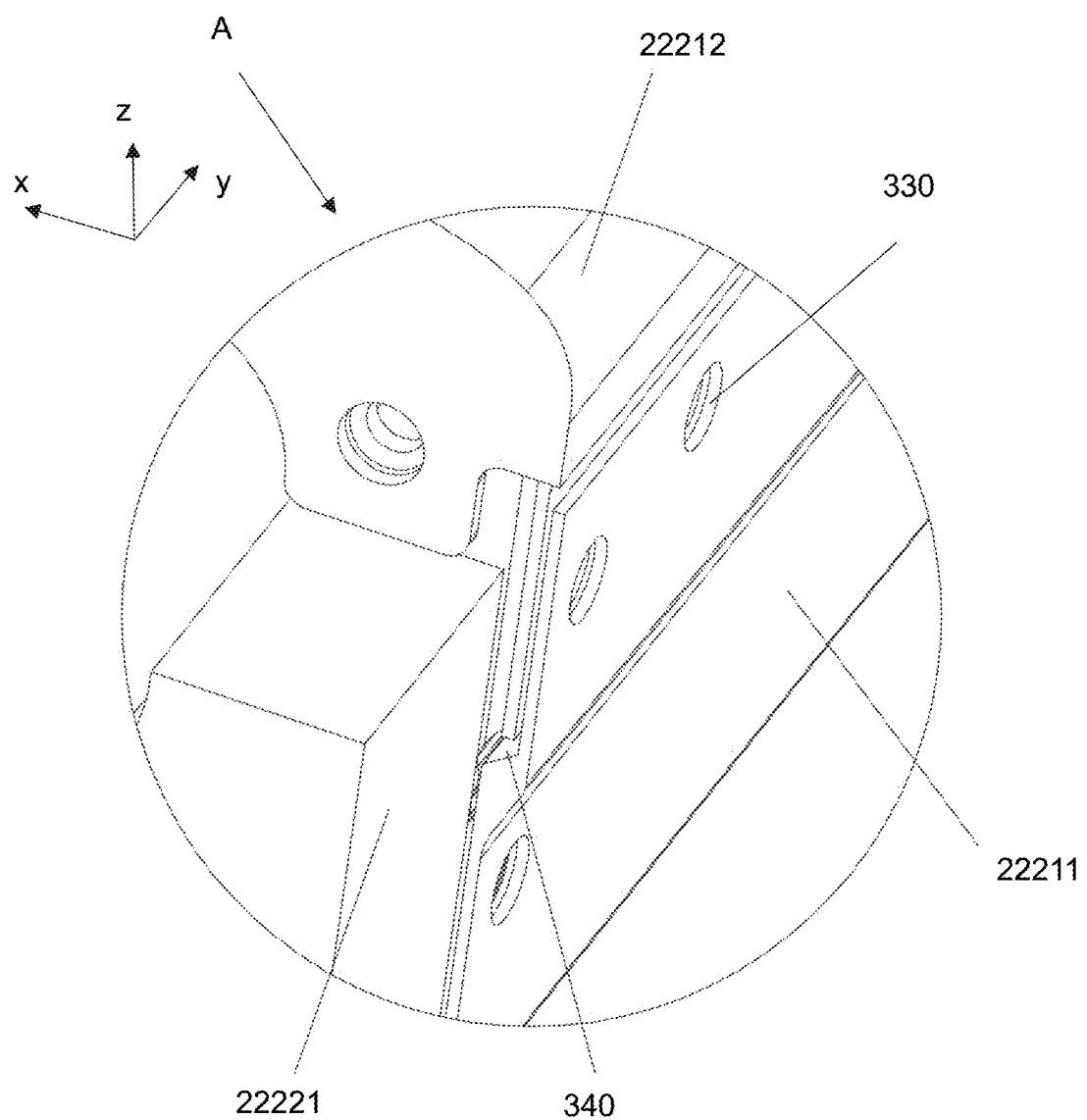
FIG. 4A is an enlarged view of the region A shown in FIG. 3 according to some embodiments of the present disclosure.
Figure 4B:
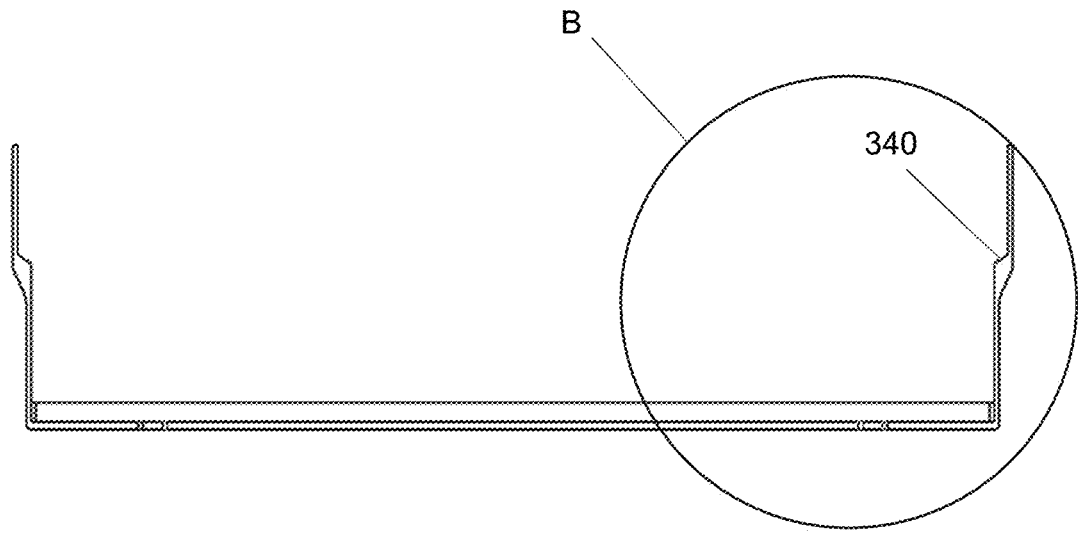
FIG. 4B is an axial sectional view of an exemplary first board according to some embodiments of the present disclosure.
Figure 4C:
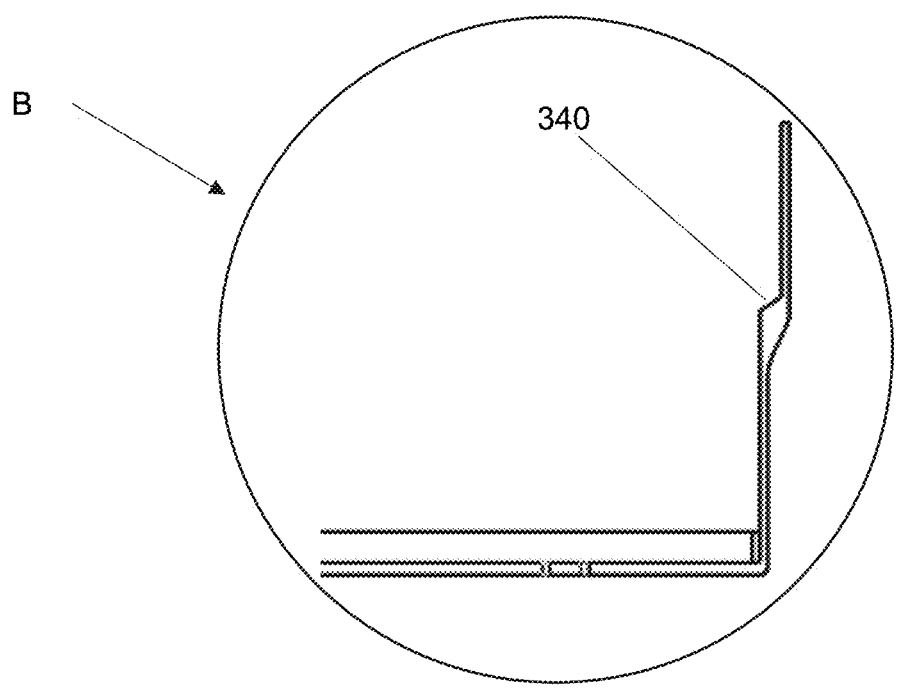
FIG. 4C is an enlarged view of the region B shown in FIG. 4B according to some embodiments of the present disclosure.
Figure 4D:
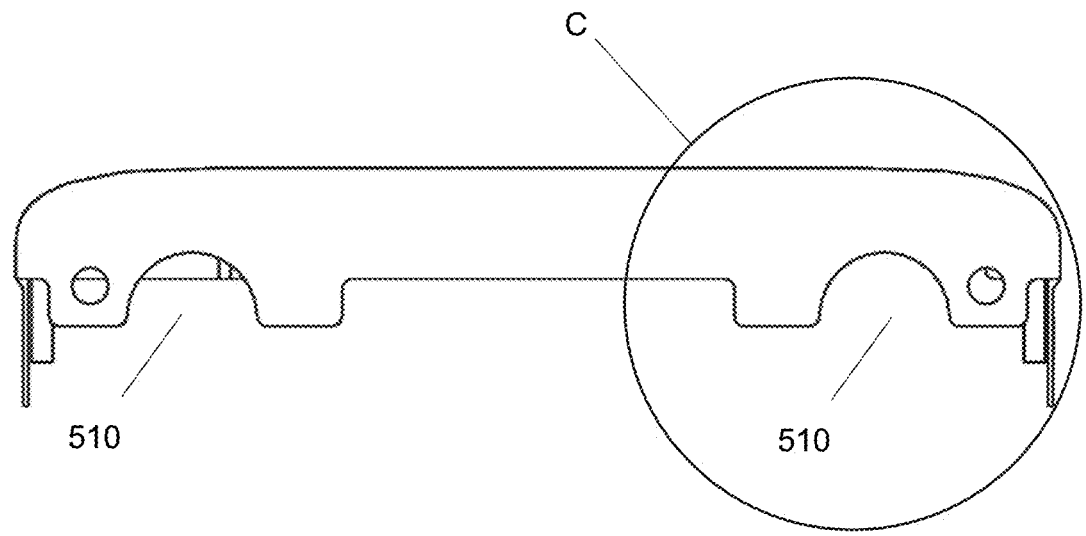
FIG. 4D is an axial sectional view of an exemplary second board according to some embodiments of the present disclosure.
Figure 4E:
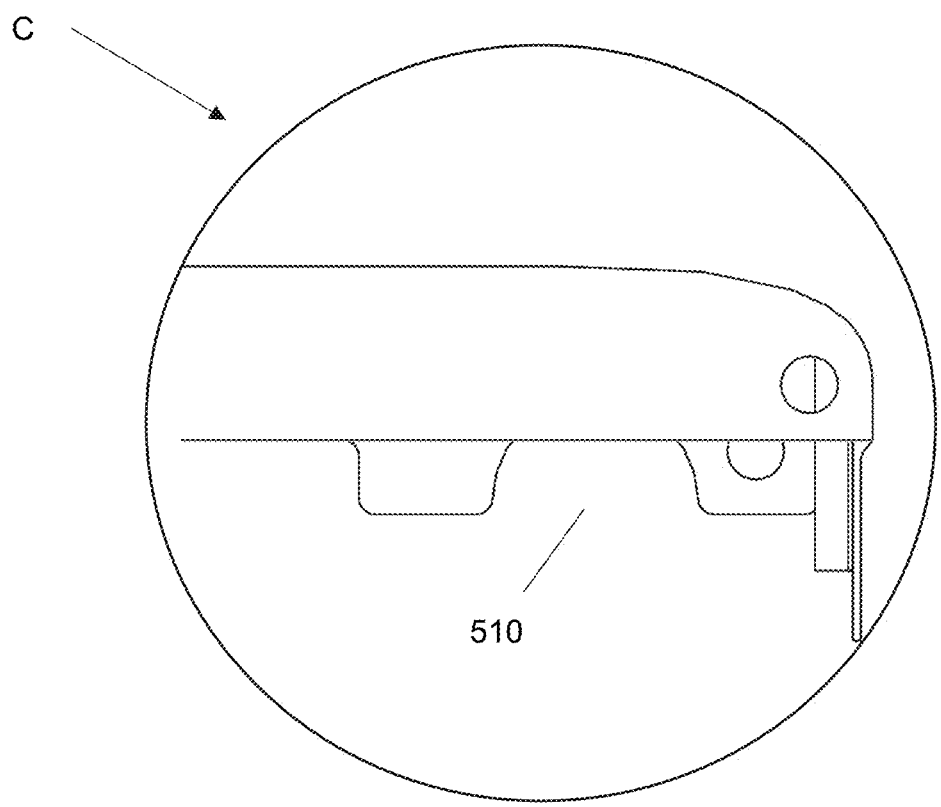
FIG. 4E is an enlarged view of the region C shown in FIG. 4D according to some embodiments of the present disclosure.
Figure 4F:
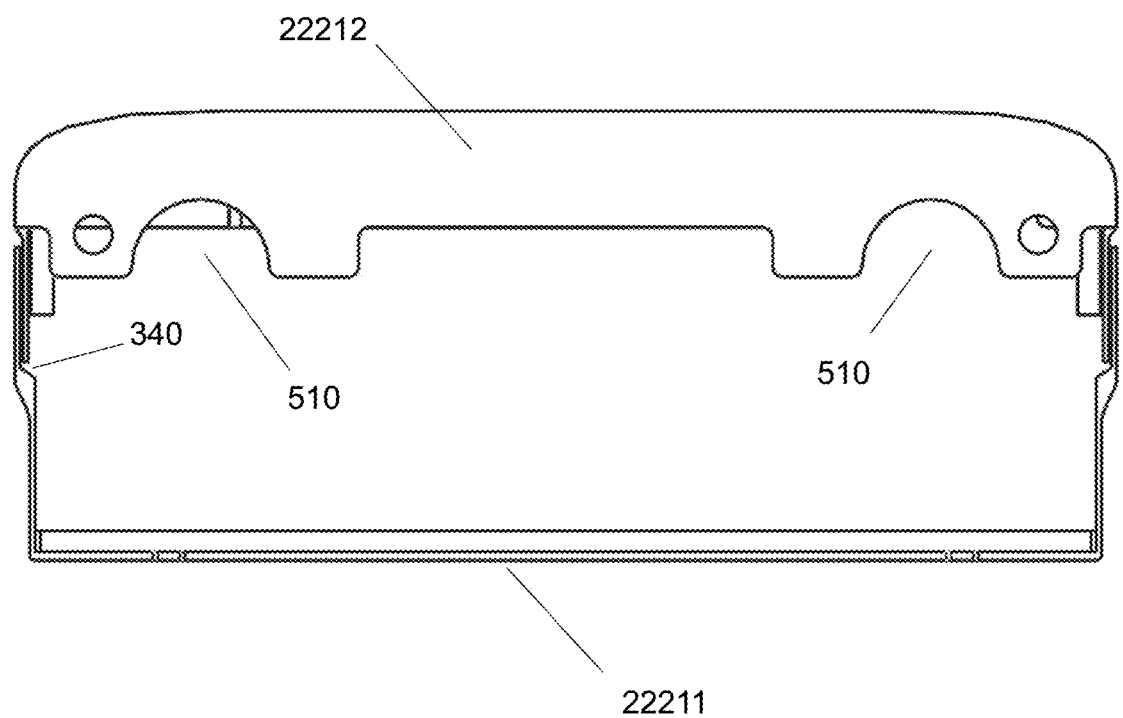
FIG. 4F is an axial sectional view of an exemplary first board and an exemplary second board according to some embodiments of the present disclosure.
Figure 5B:
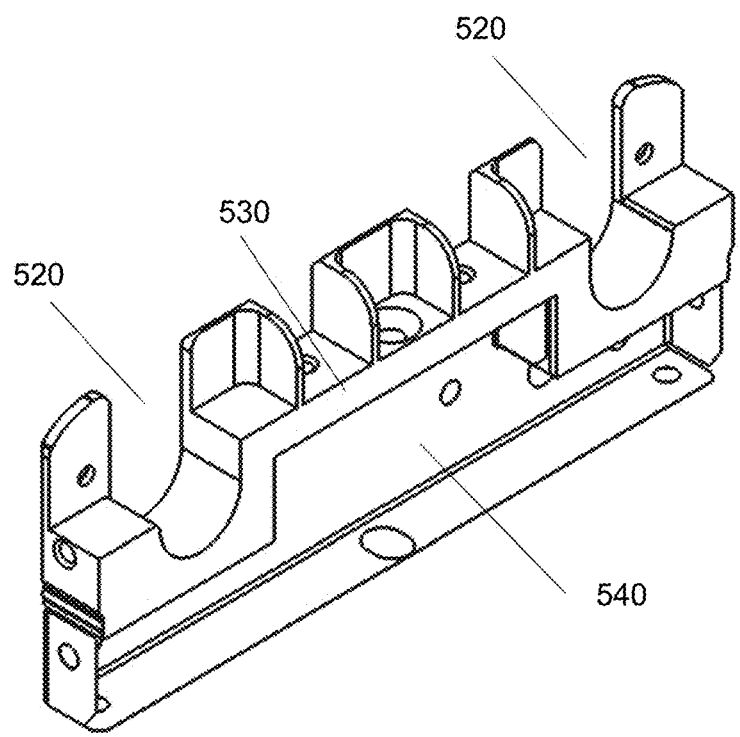
FIG. 5B is a schematic diagram illustrating an exemplary connection ring according to some embodiments of the present disclosure.
Figure 5C:
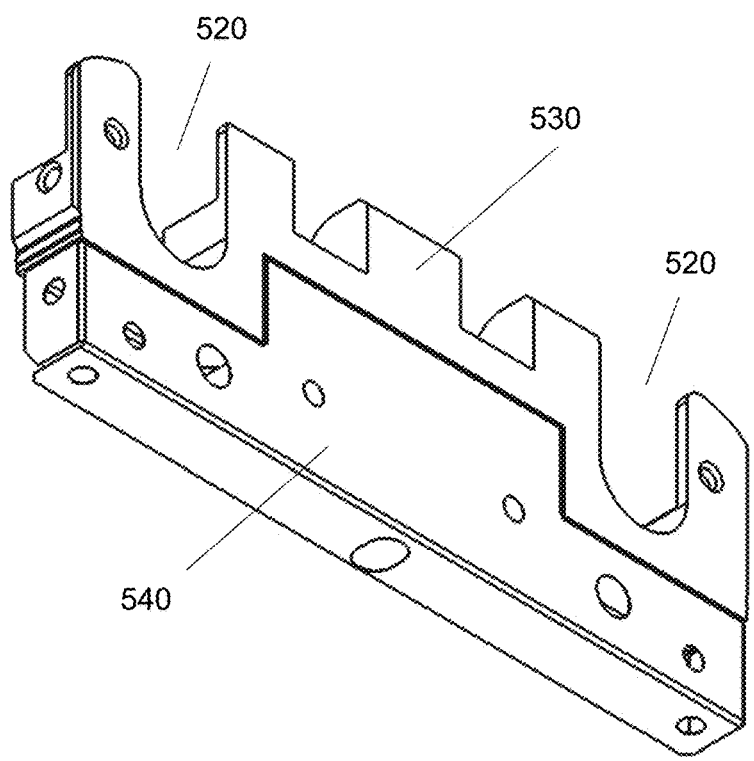
FIG. 5C is a schematic diagram illustrating an exemplary connection ring according to some embodiments of the present disclosure.

FIG. 3 is a schematic diagram illustrating an exemplary detector module according to some embodiments of the present disclosure. FIG. 4A is an enlarged view of the region A shown in FIG. 3 according to some embodiments of the present disclosure. FIG. 4B is an axial sectional view of an exemplary first board according to some embodiments of the present disclosure. FIG. 4C is an enlarged view of the region B shown in FIG. 4B according to some embodiments of the present disclosure. FIG. 4D is an axial sectional view of an exemplary second board according to some embodiments of the present disclosure. FIG. 4E is an enlarged view of the region C shown in FIG. 4D according to some embodiments of the present disclosure. FIG. 4F is an axial sectional view of an exemplary first board and an exemplary second board according to some embodiments of the present disclosure. FIG. 5A is an exploded view of the exemplary detector module shown in FIG. 3 according to some embodiments of the present disclosure. FIG. 5B is a schematic diagram illustrating an exemplary connection ring according to some embodiments of the present disclosure. FIG. 5C is a schematic diagram illustrating an exemplary connection ring according to some embodiments of the present disclosure.

In some embodiments, a detector module 300 may be a portion of the detector assembly 114. In some embodiments, the detector assembly 114 may include a plurality of detector modules 300. The detector module 300 may be configured to receive radiation rays (e.g., gamma rays) generated from a subject, provide information relating to the locations where photons are excited by the radiation rays, and/or generate electrical signals based on the radiation rays. The electrical signals may be detected and used to reconstruct an image of the subject.

As shown in FIGS. 3-5, the detector module 300 may include a crystal array 221 and a shielding component 222. The crystal array 221 may be configured to detect one or more radiation rays. In some embodiments, the crystal array 221 may include a plurality of crystal units 2211. The plurality of crystal units 2211 may be arranged in one or more rows along an X-axis direction and one or more columns along a Y-axis direction, as illustrated in FIG. 5A. In some embodiments, a size of each crystal unit 2211 may be the same or different. In some embodiments, adjacent crystal units 2211 of the plurality of crystal units 2211 may be tightly connected to each other, to reduce a spacing between the adjacent crystal units 2211, which is beneficial to improve the imaging quality of the detector module 300.

The shielding component 222 may be configured to house the crystal array 221. In some embodiments, the shielding component 222 may shield the crystal array 221 from an electromagnetic interference. For example, in a PET-MR imaging device, the shielding component 222 may shield a PET crystal array from at least part of RF signals generated by an RF coil. That is, the shielding component 222 may eliminate or reduce an interference (e.g., a coupling) between the PET crystal array and the RF coil.

In some embodiments, the shielding component 222 may include a cover 2221 and one or more connection components 2222. In some embodiments, the shielding component 222 may include a Faraday cage. As used herein, a Faraday cage may refer to an enclosure used to block electromagnetic fields. The Faraday cage may usually be formed by a continuous covering of conductive material(s), or by a mesh of such material(s). In some embodiments, the Faraday cage may be coupled to or integrated in the cover 2221 of the shielding component 222. In some embodiments, the Faraday cage may be independent from the cover 2221. For example, the Faraday cage may be set close to an outer surface or inner surface of the cover 2221. In some embodiments, the Faraday cage may be embedded in the cover 2221 and configured as an integral piece. In some embodiments, the cover 2221 and the connection component(s) 2222 may form a Faraday cage.

The cover 2221 may include an accommodating region configured to accommodate the crystal array 221. In some embodiments, the cover 2221 may be an integral piece. In some embodiments, the cover 2221 may include two or more boards, and the two or more boards may be assembled to form the cover 2221. For example, the cover 2221 may include a first board 22211 and a second board 22212, as illustrated in FIGS. 3-5. Each of the boards may have various shapes. In some embodiments, a surface of the first board 22211 and/or a surface of the second board 22212 may have a substantially rectangular shape. The first board 22211 may be positioned to face a lower surface of the crystal array 221. The second board 22212 may be positioned to face an upper surface of the crystal array 221. The lower surface and upper surface of the crystal array 221 may be parallel to the X-Y plane. In some embodiments, "a lower surface of a crystal array" may refer to a surface that is close to or faces a scanned object, and "an upper surface of the crystal array" may refer to a surface that is away from or opposite to a scanned object. In some embodiments, the first board 22211 and the second board 22212 may be oppositely connected to form the accommodating region configured to accommodate the crystal array 221. In some embodiments, the first board 22211 and/or the second board 22212 may have a U-shaped cross section, as illustrated in FIGS. 4B-4F. In some embodiments, at least one side of the first board 22211 may be bent toward the crystal array 221, or bent away from the crystal array 221 as illustrated in FIGS. 4A-4F, to form a protruding part 340. In some embodiments, a corresponding side of the second board 22212 may be abutted against the protruding part 340, as illustrated in FIG. 4F. Accordingly, a contact gap between the first board 22211 and the second board 22212 may be reduced, and the sealing performance or the integrity of the cover 2221 may further be improved.

In some embodiments, at least one of the boards may be detachable. In some embodiments, adjacent boards of the plurality of boards may be fixed together via a buckle connection, a hinged connection, a screw connection, a sliding connection, or the like, or any combination thereof. For example, the first board 22211 may be removably connected to the second board 22212. In some embodiments, the first board 22211 or the second board 22212 may be equipped with a sliding track. In some embodiments, the first board 22211 may slide along the sliding track to be removed from or installed on the second board 22212. In some embodiments, the first board 22211 may be mechanically connected to the second board 22212 via a fastener (e.g., a nail, a screw, a nut). For example, one or more screw holes 330 may be set in relative positions of the first board 22211 and the second board 22212, as illustrated in FIGS. 3-5. The first board 22211 may be mechanically connected to the second board 22212 via screws penetrating through the screw holes 330. In some embodiments, the screws may be made of an electrically conductive material. For example, the screws may be metal screws, which may facilitate a conduct of an electrical current between adjacent boards (e.g., the first board 22211 and the second board 22212), and the shielding effect of the cover 2221 may further be improved.

In some embodiments, the screw holes 330 may be distributed along one or more sides (e.g., a long side) of the board. In some embodiments, distances between adjacent screw holes 330 in the board (e.g., the first board 22211, the second board 22212) may be the same or different. For example, if a length of the board (e.g., the first board 22211, the second board 22212) is greater than a threshold, a distance between adjacent screw holes 330 in a middle portion of the board (e.g., the first board 22211, the second board 22212) may be smaller than a distance between adjacent screw holes 330 close to two ends of the board (e.g., the first board 22211, the second board 22212). This configuration may prevent a deformation of the middle portion of the board (e.g., the first board 22211, the second board 22212), and the connection between adjacent boards (e.g., the first board 22211 and the second board 22212) may be strengthened.

In some embodiments, compared with a cover with an integral structure, the structure of the cover 2221 including two or more boards may facilitate the assembly and/or the disassembly of the detector module 300. In some embodiments, it may be difficult to assemble a crystal array into the cover with the integral structure and/or disassemble the crystal array from the cover. Furthermore, during the assembly and/or the disassembly process of the crystal array, the crystal array may be damaged or scratched by edges of the cover with the integral structure.

In some embodiments, each of the boards may include a shielding layer and a base layer. The shielding layer may be configured to conduct an electrical current. The shielding layers of adjacent boards may be in contact with each other. For example, the shielding layer of the first board 22211 and the shielding layer of the second board 22212 may be in contact with each other. Accordingly, an integrity of the Faraday cage may be ensured and the shielding effect of the shielding component 222 may be improved.

In some embodiments, the shielding layer may be made of an electrically conductive material. Exemplary electrically conductive materials may include a metal (e.g., copper, silver, aluminum), a metal oxide, an alloy (e.g., stainless steel), rubber, graphite, a semiconductor, a composite polymer, or the like, or any combination thereof. The shielding layer may have any suitable two-dimensional (2D) or three-dimensional (3D) configuration. For example, the shielding layer may be implemented in any suitable configuration, e.g., a film, a mesh, or the like, or any combination thereof. Specifically, the shielding layer may be a metal film (e.g., a copper film), a metal plate, or the like. Alternatively, the shielding layer may be a metal mesh. The shielding layer implemented in the configuration of a mesh may reduce the use of the electrically conductive material, which may save cost of the shielding layer. In some embodiments, the base layer may be made of an insulation material. For example, the based layer may be made of a plastic, a glass, a ceramic, or the like.

In some embodiments, the shielding layer of the each board may be placed on an outer surface of the base layer. As used herein, "an outer surface of a base layer" may refer to a surface that is away from or opposite to a crystal array, and "an inner surface of a based layer" may refer to a surface that is close to or faces the crystal array. In some embodiments, the shielding layer (e.g., a conductive metal film) may be placed on the outer surface of the base layer by any suitable technique, e.g., hot press forming, spin coating, dip coating, screen printing, transfer coating, sputtering, physical vapor deposition, chemical vapor deposition, or the like, or any combination thereof. In some embodiments, the shielding layer (e.g., a metal mesh) may be assembled onto the outer surface of the base layer via an adhesive. Alternatively, the shielding layer of the each board may be placed on an inner surface of the base layer. In some embodiments, each board may include two shielding layers. For example, a first shielding layer may be placed on an outer surface of the base layer, while a second shielding layer may be placed on an inner surface of the base layer.

In some embodiments, the thickness of the shielding layer may be determined based on a relationship between a heat generated by eddy currents in the shielding component 222 and a shielding effect of the shielding component 222 on the electromagnetic interferences. As used herein, eddy currents may refer to loops of electrical current induced within conductors (e.g., the shielding layer) by a changing magnetic field in the conductors according to Faraday's law of induction. The thickness of the shielding layer may affect the heat generated by eddy currents in the shielding component 222 and/or the shielding effect of the shielding component 222 on the electromagnetic interferences. For example, a greater thickness of the shielding layer may cause more heat generated by the eddy currents in the shielding component 222. However, the greater thickness of the shielding layer may have a better shielding effect on the electromagnetic interferences. In some embodiments, the shielding layer may have a suitable thickness that minimizes the heat generated by eddy currents and ensures a relatively good shielding effect.

Figure 6:
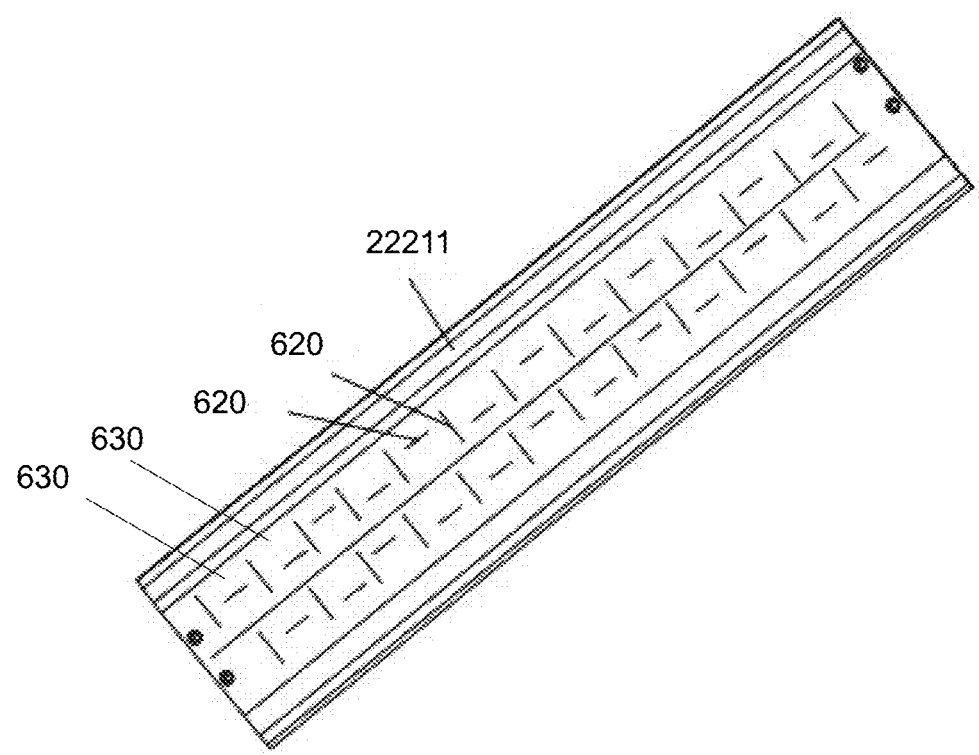
FIG. 6 is a schematic diagram illustrating an exemplary shielding layer according to some embodiments of the present disclosure.

In some embodiment, the shielding layer may include a plurality of grooves 620, as illustrated in FIG. 6. FIG. 6 is a schematic diagram illustrating an exemplary shielding layer according to some embodiments of the present disclosure. Each of the plurality of grooves 620 may penetrate an inner surface and an outer surface of the shielding layer. As used herein, "an outer surface of a shielding layer" may refer to a surface that is away from or opposite to a base layer or a crystal array, and "an inner surface of the shielding layer" may refer to a surface that is close to or faces the base layer or the crystal array. In some embodiments, the plurality of grooves 620 may be arranged on the shielding layer along different directions. For example, two or more grooves 620 may be paralleled to each other. As another example, two or more grooves 620 may form an angle (e.g., 90 degrees) with each other. Accordingly, the plurality of grooves 620 provided in the shielding layer may prevent a complete eddy current loop generated in the shielding layer, which may reduce the heat generated in the detector module 300. In some embodiments, the shielding layer may include a plurality of portions 630 associated with or corresponding to the plurality of grooves 620. Each two adjacent portions 630 of the plurality of portions 630 may be connected or contacted with each other, which may ensure that the shielding component 222 includes a complete Faraday cage.

In some embodiments, an inner surface of the base layer may include a plurality of convex portions (e.g., a first convex portion 350). The connection component 2222 may include a plurality of concave portions (e.g., a first concave portion 360) corresponding to the plurality of convex portions. In some embodiments, each convex portion may be in engaged with each concave portion. For example, the inner surface of the base layer of the first board 22211 may include a plurality of first convex portions 350, as illustrated in FIG. 5A. Two adjacent or neighboring first convex portions 350 may be spaced apart. In some embodiments, each of the plurality of first convex portions 350 may extend from a side of the first board 22211 to another side of the first board 22211 along a width direction of the first board 22211 (e.g., the X-axis direction). The connection component 2222 may include a plurality of first concave portions 360 corresponding to the plurality of first convex portions 350. As another example, the inner surface of the base layer of the second board 22212 may include a plurality of second convex portions (not shown in FIG. 5A). The connection component 2222 (e.g., the connection ring 22222) may include a plurality of second concave portions (not shown in FIG. 5A) corresponding to the plurality of second convex portions.

Because a length of the crystal array 221 along the Y-axis direction is relatively large and a thickness of the crystal array 221 along the Z-axis direction is relatively thin, the cover 2221 may need to have a relatively high strength and/or stability to protect the crystal array 221. The plurality of convex portions (also be considered as reinforcing components) provided on the board (e.g., the first board 22211, the second board 22212) may strengthen the rigidity of the board, and also prevent the deformation of the board.

In some embodiments, an inner surface of the base layer of the first board 22211 (or the second board 22212) may include a plurality of concave portions. The connection component 2222 may include a plurality of convex portions corresponding to the plurality of concave portions.

In some embodiments, a number (or count) of the convex portions and/or a number (or count) of the concave portions configured on the inner surface of the base layer of the first board 22211 (or the second board 22212) may be determined based on a structure of the detector module 300 (e.g., a size of the connection component 2222). If the size of the connection component 2222 is relatively large, a number (or count) of the convex portions and/or concave portions configured on the inner surface of the base layer may be relatively large. For example, the inner surface of the base layer of the first board 22211 may include three convex portions 350, as illustrated in FIG. 5A.

The connection component 2222 may be configured to connect the detector module 300 to an imaging device (e.g., the imaging device 110). The connection component 2222 may be operably coupled to the crystal array 221 and the cover 2221. For example, as illustrated in FIGS. 3 and 5, the detector module 300 may include two connection components 2222 mounted on two ends of the crystal array 221, respectively. Each connection component 2222 may be connected to an end of the first board 22211 and an end of the second board 22212.

In some embodiments, the detector module 300 may be connected to a gantry (e.g., the gantry 112) of the imaging device (e.g., the imaging device 110) via the connection component 2222. In some embodiments, the detector module 300 may be connected to a supporting component (e.g., a supporting component 750 as illustrated in FIG. 7) of a cooling assembly (e.g., the cooling assembly 230, a cooling assembly 700 as illustrated in FIG. 7) of the imaging device (e.g., the imaging device 110) via the connection component 2222. In some embodiments, the connection component 2222 may be connected to the imaging device (e.g., the gantry, the supporting component) via a buckle connection, a hinged connection, a screw connection, a sliding connection, or the like, or any combination thereof. For example, screw holes may be configured in relative positions of the connection component 2222 and the gantry. The connection component 2222 may be mechanically connected to the gantry via screws penetrating through the screw holes.

In some embodiments, the connection component 2222 may include a connection block 22221, and at least one connection ring 22222 as illustrated in FIGS. 5B-5C. The connection block 22221 may be operably coupled to the crystal array 221. For example, the connection block 22221 may be connected to an end of the crystal array 221. In some embodiments, the connection block 22221 may be connected to an end of the cover 2221. The at least one connection ring 22222 may be sleeved on the connection block 22221. In some embodiments, the connection block 22221 may be made of an insulation material (e.g., a plastic). In some embodiments, the at least one connection ring 22222 may be made of an electrically conductive material (e.g., a metal, a metal oxide, an alloy). For example, the at least one connection ring 22222 may be made of copper. The at least one connection ring 22222 may be connected or contacted with the shielding layer of the cover 2221. Accordingly, the cover 2221 and the connection component 2222 may form a complete Faraday cage.

In some embodiments, the connection ring 22222 may include a first component 530 and a second component 540, as illustrated in FIGS. 5B and 5C. In some embodiments, the first component 530 may have a relatively high strength and/or stability to provide a stable support for one or more components (e.g., the inlet tube 310, and an outlet tube 320) of the detector module 300. In some embodiments, the thickness of the first component 530 along the Y-axis direction may be greater than the thickness of the second component 540 along the Y-axis direction. A smaller thickness of the second component 540 may cause less heat generated by the eddy currents in the detector module 300. In some embodiments, the second component 540 may be formed by benting a thin metal sheet (e.g., a copper sheet).

In some embodiments, a number (or count) of the connection components 2222 may be determined based on an assembly requirement of the detector module 300 on the imaging device (e.g., the imaging device 110). For example, the number (or count) of the connection components 2222 may be 1, 2, 3, 4, 5, 6, or the like.

In some embodiments, the detector module 300 may include a cooling component 380 configured to cool the crystal array 221. In some embodiments, the cooling component 380 may be configured inside the cover 2221. For example, the cooling component 380 may be configured between the second board 22212 and the crystal array 221. In some embodiments, the cooling component 380 may include a supporting board 390, at least one delivering tube 370, an inlet tube 310, and an outlet tube 320. The supporting board 390 may be configured to support the at least one delivering tube 370. In some embodiments, the at least one delivering tube 370 may be wanderingly embedded in the supporting board 390. The at least one delivering tube 370 may be configured to deliver a cooling medium to the adjacency of the crystal array 221 and absorb heat produced by the crystal array 221.

The inlet tube 310 and the outlet tube 320 may be in fluid communication with the at least one delivering tube 370. In some embodiments, the cooling medium cooled by a cooling source may flow through the inlet tube 310 to the at least one delivering tube 370 and absorb heat from the crystal array 221. Then a heat-laden cooling medium may flow through the outlet tube 320 and return to the cooling source to be cooled. This process may be repeated (e.g., the cooling medium may circulate between the cooling source and the cooling component 380) to cool the crystal array 221. More descriptions of the cooling process may be found elsewhere in the present disclosure (e.g., FIGS. 7-15, and descriptions thereof).

In some embodiments, a plurality of first passages 510 may be formed on one or more boards (e.g., the second board 22212) of the cover 2221, as illustrated in FIGS. 4D, 4E, 4F, and 5A. A plurality of second passages 520 corresponding to the plurality of first passages 510 may be formed on the connection component 2222 (e.g., the connection ring 22222), as illustrated in FIGS. 5A-5C. Each pair of first passage 510 and corresponding second passage 520 may form a passage configured to accommodate the inlet tube 310 or the outlet tube 320.

In some embodiments, a shielding element (not shown in FIG. 5A) may be configured on a contact surface of the inlet tube 310 and a corresponding passage and/or a contact surface of the outlet tube 320 and a corresponding passage, to improve the shielding effect of the shielding component 222. In some embodiments, at least a portion of the inlet tube 310 and/or the outlet tube 320 may be made of an electrically conductive material.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the inlet tube 310, the outlet tube 320, and the at least one delivering tube 370 may be configured as an integral piece. In some embodiments, the inlet tube 310 and the outlet tube 320 may be unnecessary. The cooling medium may include a phase-change material. The delivering tube 370 may be configured to house the phase-change material. The phase-change material may change its phase according to its temperature. The phase-change material may absorb or release heat when it changes its phase. In some embodiments, if the cooling medium includes the phase-change material, the cooling source may be unnecessary, or the cooling medium may not circulate between the cooling component 380 and the cooling source.

In some embodiments, the phase-change material housed in the delivering tube 370 may have a desirable or low boiling point. When the temperature increases and exceeds its boiling point, the phase-change material may absorb heat and change its phase (e.g., vaporization). When the temperature decreases and falls below its boiling point, the phase-change material may release heat and change its phase (e.g., condensation). In some embodiments, the phase-change material housed in the delivering tube 370 may have a desirable or low melting point. When the temperature increases and exceeds its melting point, the phase-change material may absorb heat and change its phase (e.g., melting). When the temperature decreases and falls below its melting point, the phase-change material may release heat and change its phase (e.g., freezing).

FIGS. 7 and 8 are schematic diagrams illustrating an exemplary cooling assembly according to some embodiments of the present disclosure. In some embodiments, a cooling assembly 700 may be an example of the cooling assembly 116 (or the cooling assembly 230) or a portion of the cooling assembly 116 (or the cooling assembly 230). As shown in FIGS. 7 and 8, the cooling assembly 700 may include a separator 710, a plurality of delivering tubes (not shown in FIGS. 7 and 8), and a collector 720. In some embodiments, the cooling assembly 700 may further include a supporting component 750.

The separator 710 may be configured to separate or distribute a cooling medium into the plurality of delivering tubes (e.g., a delivering tube 370 as illustrated in FIG. 5A). In some embodiments, the delivering tubes may be embedded in the detector assembly (see FIG. 5A). The separator 710 may include a separation main tube 711, at least one separation chamber (e.g., a plurality of separation chambers 713 as illustrated in FIG. 9), and a plurality of separation branch tubes 712. The separation main tube 711 may be in fluid communication with the at least one separation chamber. The plurality of separation branch tubes 712 may be in fluid communication with the at least one separation chamber. For example, a separation branch tube 712 may be in fluid communication with one or more of the at least one separation chamber. As another example, one or more separation branch tubes 712 may be in fluid communication with one of the at least one separation chamber.

The separation main tube 711 may be configured to deliver the cooling medium from a cooling source to the at least one separation chamber. In some embodiments, the separation main tube 711 may be connected to the cooling source (e.g., via a tube). The cooling source may be configured to generate, and/or process (e.g., cool down) the cooling medium, and/or drive the cooling medium to flow. In some embodiments, the separation main tube 711 may include a first switch or valve configured to control a flow (e.g., a flow-off and/or a flow rate) of the cooling medium in the separation main tube 711. For example, if the first switch or valve is turned on, the cooling medium may flow from the cooling source to the at least one separation chamber via the separation main tube 711. A flow rate and/or a flow amount of the cooling medium in the separation main tube 711 may be adjusted by the first switch or valve. If the first switch or valve is turned off, the cooling medium cannot flow from the cooling source to the separator 710. In some embodiments, the separator 710 may include any suitable number of separation main tubes 711, e.g., 1, 2, 3, 4, or more.

The at least one separation chamber may be configured to store the cooling medium. In some embodiments, the at least one separation chamber may include one or more levels (or stages) of separation chambers. In some embodiments, the at least one separation chamber may include at least two levels of separation chambers. For example, a number (or count) of levels of separation chambers may be 2, 3, 4, 5, 10, or the like. In some embodiments, the number (or count) of levels of separation chambers may be determined based on an amount and/or a pressure of the cooling medium circulating in the cooling assembly 700. For example, if the amount, flow rate, and/or pressure of the cooling medium in the cooling assembly 700 is relatively high, relatively great levels of separation chambers may be used.

In some embodiments, the at least one separation chamber may include one or more first-stage separation chambers (e.g., a first-stage separation chamber 7131 as illustrated in FIG. 9), and one or more last-stage separation chambers (e.g., a plurality of last-stage separation chambers 7133 as illustrated in FIG. 9). Each of the one or more first-stage separation chambers may be in fluid communication with at least one of the one or more last-stage separation chambers. The separation main tube 711 may be in fluid communication with the one or more first-stage separation chambers. In some embodiments, each separation branch tube 712 may be in fluid communication with one of the one or more last-stage separation chambers. For example, the one or more last-stage separation chambers may include a plurality of separation grooves (e.g., a plurality of separation grooves 714 as illustrated in FIGS. 9-13). In some embodiments, each of the one or more first-stage separation chambers may be in fluid communication with one or more of the plurality of separation grooves. More descriptions of the separation grooves may be found elsewhere in the present disclosure (e.g., FIGS. 9-13, and descriptions thereof).

In some embodiments, the at least one separation chamber may further include one or more intermediate-stage separation chambers between the one or more first-stage separation chambers and the one or more last-stage separation chambers. One of the one or more intermediate-stage separation chambers may be in fluid communication with at least one of the one or more first-stage separation chambers and at least one of the one or more last-stage separation chambers.

In some embodiments, an upper-stage separation chamber of the at least one separation chamber may be configured to deliver a portion of the cooling medium into a (e.g., each) lower-stage separation chamber of the at least one separation chamber, in response to an amount of the cooling medium in the upper-stage separation chamber exceeding a threshold. For example, a first-stage separation chamber (e.g., the first-stage separation chamber 7131 as illustrated in FIG. 9) may deliver a portion of the cooling medium into a (e.g., each) second-stage separation chamber (e.g., the last-stage separation chamber 7133 as illustrated in FIG. 9), in response to an amount of the cooling medium in the first-stage separation chamber (e.g., the first-stage separation chamber 7131) exceeding a threshold. The threshold may be manually set by a user of the imaging system 100 or determined by one or more components (e.g., the processing device 120) of the imaging system 100. In some embodiments, the threshold may be associated with a structure and/or size of the at least one separation chamber. In some embodiments, different separation chambers may correspond to a same threshold. In some embodiments, different separation chambers may correspond to different thresholds. In some embodiments, the threshold corresponding to a separation chamber may be associated with a volume of the separation chamber. For example, the threshold may be in a range of ⅓ to ¾ of the volume of the corresponding separation chamber. In some embodiments, the threshold corresponding to a separation chamber may be associated with a structure of the at least one separation chamber.

The plurality of separation branch tubes 712 may be configured to deliver the cooling medium from the at least one separation chamber to the plurality of delivering tubes. In some embodiments, a number (or count) of the separation branch tubes 712 may be the same as a number (or count) of the delivering tubes. For example, each separation branch tube 712 of the plurality of separation branch tubes 712 may correspond to a delivering tube of the plurality of delivering tubes. In some embodiments, the number (or count) of the separation branch tubes 712 may be different from the number (or count) of the delivering tubes. For example, each separation branch tube 712 of the plurality of separation branch tubes 712 may correspond to two or more delivering tubes of the plurality of delivering tubes. As another example, two or more separation branch tubes 712 of the plurality of separation branch tubes 712 may correspond to one delivering tube of the plurality of delivering tubes.

The delivering tube may be configured to deliver a portion of the cooling medium to a target portion of an imaging device (e.g., the imaging device 110, the imaging device 200). The target portion may include one or more components (e.g., one or more detector modules 300) of the imaging device. In some embodiments, the delivering tube (e.g., the delivering tube 370 as illustrated in FIG. 5A) may pass through the target portion of the imaging device to deliver the portion of the cooling medium to the target portion of the imaging device or the adjacency of the target portion. The cooling medium may absorb heat from the target portion of the imaging device. After the cooling medium absorbs heat from the target portion, a heat-laden cooling medium may be generated.

The collector 720 may be configured to collect heat-laden cooling medium from the target portion(s) of the imaging device. In some embodiments, the collector 720 may include a collection main tube 721 and a plurality of collection branch tubes 722. In some embodiments, each collection branch tube 722 of the plurality of collection branch tubes 722 may be in fluid communication with at least one delivering tube of the plurality of delivering tubes.

The plurality of collection branch tubes 722 may be configured to deliver the heat-laden cooling medium from the plurality of delivering tubes to the collection main tube 721. In some embodiments, a delivering tube may include two ends. A first end of the delivering tube may be coupled to at least one separation branch tube 712 to form a fluid communication with the separation branch tube 712, while a second end of the delivering tube may be coupled to at least one collection branch tube 722 to form a fluid communication with the collection branch tube 722. The collection main tube 721 may be configured to deliver the heat-laden cooling medium from the plurality of collection branch tubes 722 to the cooling source. The cooling source may absorb heat from the heat-laden cooling medium, and then the heat-laden cooling medium may be cooled down. Accordingly, the cooling medium may be recycled. In some embodiments, the collection main tube 721 may include a second switch or valve configured to control a flow (e.g., a flow-off and/or a flow rate) of the heat-laden cooling medium in the collection main tube 721. For example, if the second switch or valve is turned on, the heat-laden cooling medium may flow from the plurality of collection branch tubes 722 to the cooling source via the collection main tube 721. A flow rate and/or a flow amount of the heat-laden cooling medium in the collection main tube 721 may be adjusted by the second switch or valve. If the second switch or valve is turned off, the heat-laden cooling medium cannot flow from the collector 720 to the cooling source. In some embodiments, the collector 720 may include any suitable number of collection main tubes 721, e.g., 1, 2, 3, 4, or more.

In some embodiments, the collector 720 may further include at least one collection chamber (not shown in FIGS. 7 and 8) in fluid communication with the collection main tube 721 and the plurality of collection branch tubes 722. In some embodiments, the collector 720 may include only one level of collection chamber. For example, the collector 720 may include only one collection chamber in fluid communication with the collection main tube 721 and the plurality of collection branch tubes 722. In some embodiments, a structure of the collector 720 may be the same as a structure of the separator 710. For example, the at least one collection chamber may include at least two levels (or stages) of collection chambers. The at least two levels of separation chambers may include one or more first-stage collection chambers, one or more intermediate-stage collection chambers, and/or one or more last-stage collection chambers. One of the one or more intermediate-stage collection chambers may be in fluid communication with at least one of the one or more first-stage collection chambers and at least one of the one or more last-stage collection chambers. The collection main tube 721 may be in fluid communication with the one or more first-stage collection chambers. The each collection branch tube 722 may be in fluid communication with at least one of the one or more last-stage collection chambers. Accordingly, if the separator 710 and the collector 720 have a same structure, the separator 710 and the collector 720 may be manufactured by a same process, which may save a manufacturing cost. In addition, when the cooling assembly 700 is assembled, it is not necessary to distinguish the separator 710 and the collector 720, and the assembly process may be simplified.

In some embodiments, the structure of the collector 720 may be different from the structure of the separator 710. For example, the collector 720 may include the collection main tube 721, a collection chamber (e.g., an annular collection chamber), and the plurality of collection branch tubes 722. The annular collection chamber may collect the heat-laden cooling medium from the plurality of collection branch tubes 722 and deliver the heat-laden cooling medium to the collection main tube 721.

The supporting component 750 may be configured to support a plurality of detector modules 740 of a detector assembly (e.g., the detector assembly 114, the detector assembly 220). In some embodiments, the plurality of detector modules 740 may be arranged on an inner surface of the supporting component 750 circumferentially to form a plurality of detector rings along an axial direction of the cooling assembly 700. For example, the detector module 740 may be mounted on the inner surface of the supporting component 750 via a connection component (e.g., the connection component 2222 as illustrated in FIGS. 3 and 5) of the detector module 740 as described elsewhere in the present disclosure.

In some embodiments, the separator 710 may have any suitable shape. The shape of the separator 710 may be the same as or different from the shape of the detector assembly (e.g., the detector assembly 114). In some embodiments, a cross section of the separator 710 may have a closed structure. For example, the cross section of the separator 710 (in a plane perpendicular to the axial direction of the detector assembly) may have a ring shape as illustrated in FIGS. 7 and 8, a hollow square shape, or the like. In some embodiments, the separator 710 may have a curved shape or a flat shape. In some embodiments, the shape of the collector 720 may be the same as or different from the shape of the separator 710.

In some embodiments, the separator 710 and/or the collector 720 may be operably coupled to the target portion (e.g., the detector assembly 114) of the imaging device (e.g., the imaging device 110). In some embodiments, the separator 710 and the collector 720 may be disposed on a same side of the target portion(s) of the imaging device. For example, the separator 710 may be disposed on an outer surface of the collector 720. As another example, the separator 710 may be disposed on an inner surface of the collector 720. As still another example, the separator 710 and the collector 720 may be disposed separately on the same side of the target portion(s). In some embodiments, the separator 710 and the collector 720 may be disposed on different sides of the target portion(s) of the imaging device, as illustrated in FIGS. 7 and 8. In this situation, one end of the detector assembly may be mounted on or coupled to an inner surface (or an outer surface) of the separator 710 and/or the other end of the detector assembly may be mounted on or coupled to the inner surface (or the outer surface) of the collector 720. In some embodiments, the separator 710 and/or the collector 720 may be disposed surrounding the target portion(s) of the imaging device. For example, the separator 710 and/or the collector 720 may be disposed on an outer surface (or an inner surface) of the target portion(s) of the imaging device.

In some embodiments, the separator 710 may include a plurality of separation outlets. The plurality of separation branch tubes 712 may be mounted on or coupled to the separator 710 via the plurality of separation outlets. In some embodiments, a number (or count) of the separation outlets may be the same as the number (or count) of the separation branch tubes 712. For example, each separation branch tube 712 of the plurality of separation branch tubes 712 may correspond to a separation outlet of the plurality of separation outlets. In some embodiments, a separation connector 7121 may be mounted on or coupled to a separation outlet of the plurality of separation outlets. The separation branch tube 712 may be mounted on or coupled to the separation connector 7121 to from a fluid communication with the at least one separation chamber, which may avoid a leakage of the cooling medium.

In some embodiments, the collector 720 may include a plurality of collection inlets. The plurality of collection branch tubes 722 may be mounted on or coupled to the collector 720 via the plurality of collection inlets. In some embodiments, a number (or count) of the collection inlets may be the same as the number (or count) of the collection branch tubes 722. For example, each collection branch tube 722 of the plurality of collection branch tubes 722 may correspond to a collection inlet of the plurality of collection inlets. In some embodiments, a collection connector 7221 may be mounted on or coupled to a collection outlet of the plurality of collection inlets. The collection branch tube 722 may be mounted on or coupled to the collection connector 7221 to from a fluid communication with the at least one collection chamber, which may avoid a leakage of the cooling medium.

In some embodiments, a connection between a separation branch tube 712 and a delivering tube and a connection between a delivering tube and a collection branch tube 722 may be disposed on a same side of the target portion (e.g., the detector module 740) of the imaging device (e.g., the imaging device 110). For example, as illustrated in FIGS. 5, 7 and 8, the separation branch tube 712 may be connected to the inlet tube 310 to form a fluid communication with the delivering tube 370. The collection branch tube 722 may be connected to the outlet tube 320 to form a fluid communication with the delivering tube 370. The connection between the separation branch tube 712 and the delivering tube 370 and the connection between the delivering tube 370 and the collection branch tube 722 may be disposed on the same side of the detector module 300. In this situation, an inflow and an outflow of the cooling medium may be achieved on the same side of the target portion(s) of the imaging device, which may facilitate the maintenance of the cooling assembly 700. In some embodiments, the connection between a separation branch tube 712 and a delivering tube and the connection between a delivering tube and a collection branch tube 722 may be disposed on different sides of the target portion(s) of the imaging device (not shown).

In some embodiments, the separation main tube 711, one or more of the plurality of separation branch tubes 712, one or more of the plurality of delivering tubes, the collection main tube 721, one or more of the plurality of collection branch tubes 722, or a portion thereof (e.g., a bending portion of a tube), may be made of a flexible material (e.g., a polymer flexible material). The flexible material may facilitate a connection between two adjacent tubes (e.g., a connection between the separation branch tube 712 and the delivering tube, a connection between the delivering tube and the collection branch tube 722, a connection between the collection branch tube 722 and the collection main tube 721), which may avoid a damage of the tube(s).

For illustration purposes, a cooling process is taken as an example. Specifically, a cooling medium generated by a cooling source may flow to the at least one separation chamber via the separation main tube 711. The at least one separation chamber may include a plurality of levels of separation chambers, for example, one or more first-stage separation chambers, one or more second-stage separation chambers, one or more third-stage separation chambers, one or more fourth-stage separation chambers, and one or more fifth-stage separation chambers (i.e., one or more last-stage separation chambers). The cooling medium may flow sequentially from the one or more first-stage separation chambers to the one or more second-stage separation chambers, the one or more third-stage separation chambers, the one or more fourth-stage separation chambers, and the one or more last-stage separation chambers. The cooling medium may then flow from the one or more last-stage separation chambers to the plurality of separation branch tubes 712, and further to the plurality of delivering tubes. A portion of the cooling medium in each of the plurality of delivering tubes may absorb heat from a target portion (e.g., the detector module 740) of the imaging device (e.g., the imaging device 110). After the heat of the target portion is absorbed by the cooling medium, the cooling medium may convert to a heat-laden cooling medium. The heat-laden cooling medium may flow from the plurality of delivering tubes to the plurality of collection branch tubes 722, and then be collected by the collection main tube 721. The collection main tube 721 may deliver the heat-laden cooling medium back to the cooling source. The cooling source may cool down the heat-laden cooling medium and generate the cooling medium. This process may be repeated to cool the plurality of detector modules 740 in the imaging device.

Figure 16:
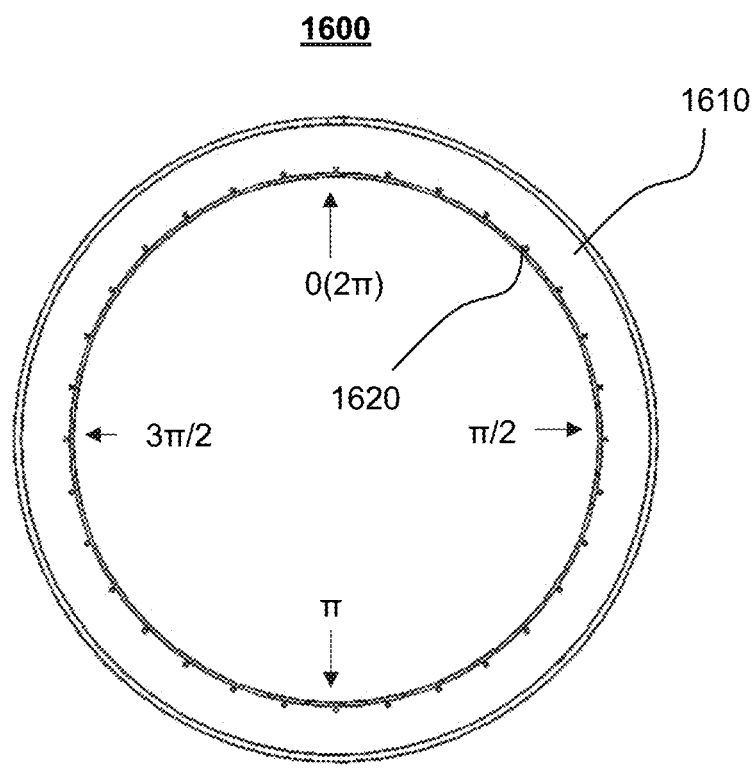
FIG. 16 is a schematic diagram illustrating an exemplary separator according to some embodiments of the present disclosure.
Figure 17:
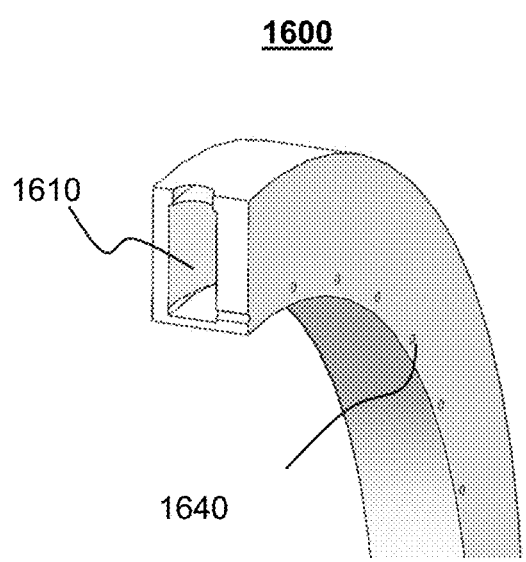
FIG. 17 is a schematic diagram illustrating an exemplary separator according to some embodiments of the present disclosure.
Figure 19:
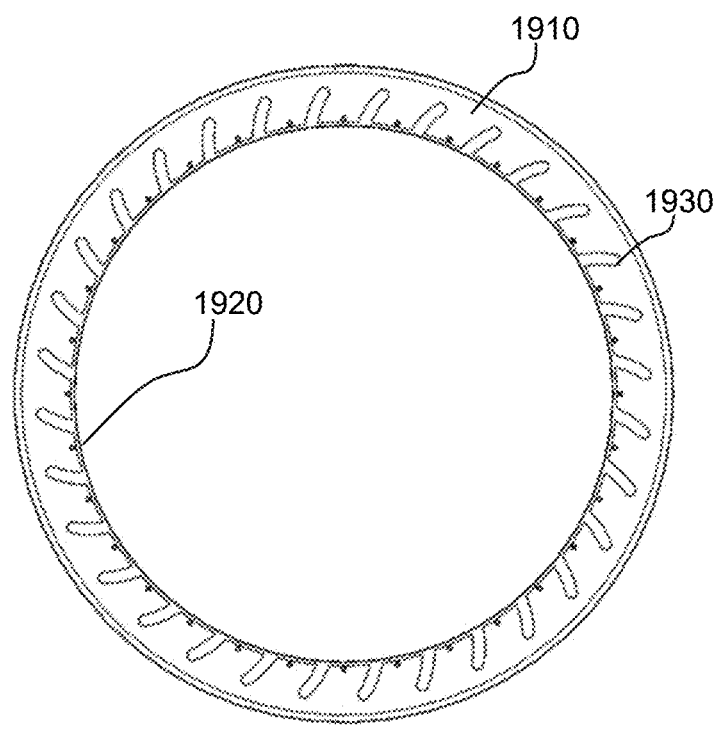
FIG. 19 is a schematic diagram illustrating an exemplary separator according to some embodiments of the present disclosure.
Figure 20:
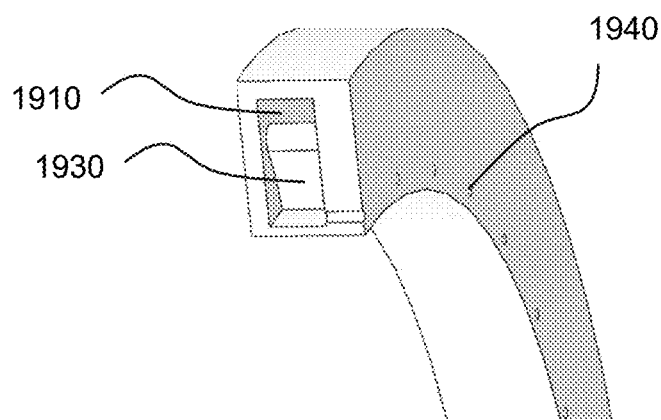
FIG. 20 is a schematic diagram illustrating an exemplary separator according to some embodiments of the present disclosure.
Figure 21:
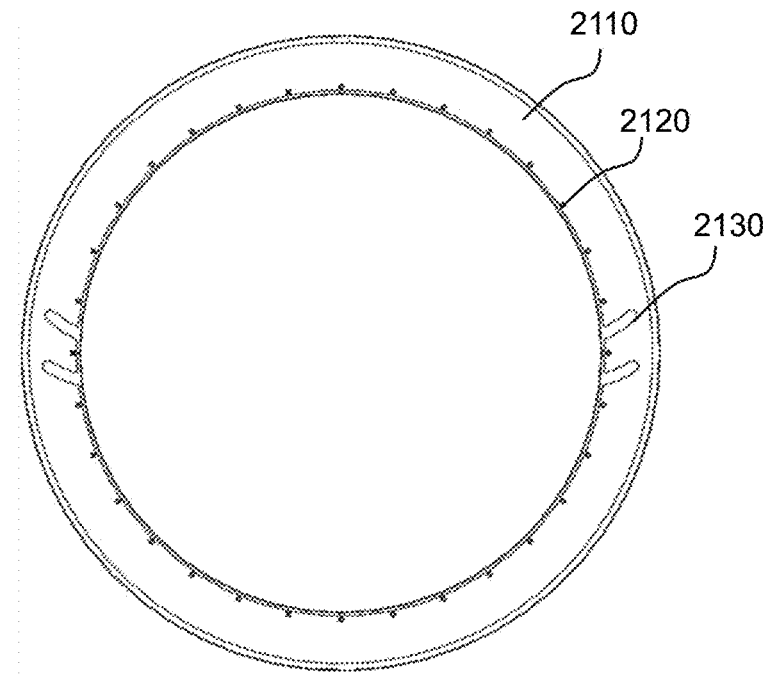
FIG. 21 is a schematic diagram illustrating an exemplary separator according to some embodiments of the present disclosure.
Figure 22:
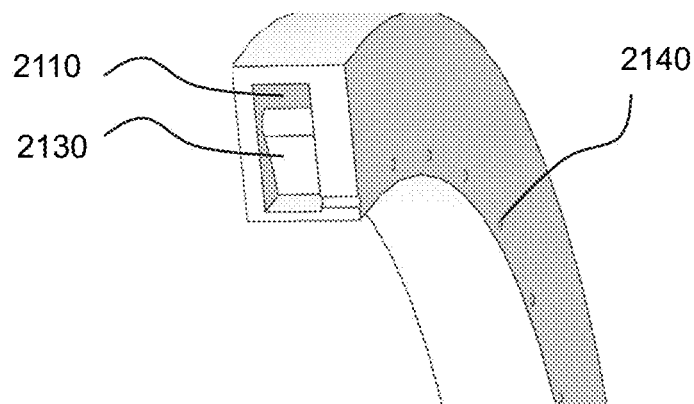
FIG. 22 is a schematic diagram illustrating an exemplary separator according to some embodiments of the present disclosure.

According to some embodiments of the present disclosure, the configuration of the at least two levels of separation chambers may ensure an uniform flow distribution of the cooling medium in the one or more last-stage separation chambers, and accordingly may guarantee that a flow amount and/or a flow rate of the cooling medium in each of the plurality of separation branch tubes is substantially the same. Specifically, assuming that a separator (e.g., a separator 1600 as illustrated in FIGS. 16 and 17, a separator 1900 as illustrated in FIGS. 19 and 20, a separator 2100 as illustrated in FIGS. 21 and 22) only includes one or more first-stage separation chambers, as illustrated in FIGS. 16-22, when a cooling medium flows from a cooling source to a separation main tube, a flow amount or a flow rate of the cooling medium in the separation main tube may not be sufficient to ensure that the cooling medium flows to each first-stage separation chamber of the one or more first-stage separation chambers uniformly. The cooling medium in the each first-stage separation chamber may then flow to a separation branch tube of the plurality of separation branch tubes. A flow amount and/or a flow rate of the cooling medium in the each separation branch tube of the plurality of separation branch tubes may also be ununiform.

With the configuration of the at least two levels of separation chambers, the cooling medium in the one or more first-stage separation chambers cannot flow to the plurality of separation branch tubes directly. After the cooling medium flows from the one or more first-stage separation chambers to the one or more last-stage separation chambers, the flow amount of the cooling medium in each last-stage separation chamber may be uniform and sufficient to ensure that the cooling medium flows to each separation branch tube 712 of the plurality of separation branch tubes 712 uniformly. The cooling medium may be separated or distributed in the plurality of separation branch tubes 712 uniformly, and a circumferential flow gradient may be eliminated. Therefore, temperature gradients among the plurality of detector modules 740 may also be eliminated, the temperature of each detector module 740 may be balanced, which may ensure a consistent and stable response of the plurality of detector modules 740 in the detector assembly. In addition, the imaging quality of the imaging device may be improved, which may facilitate diagnosis of the scanned object.

Figure 15:
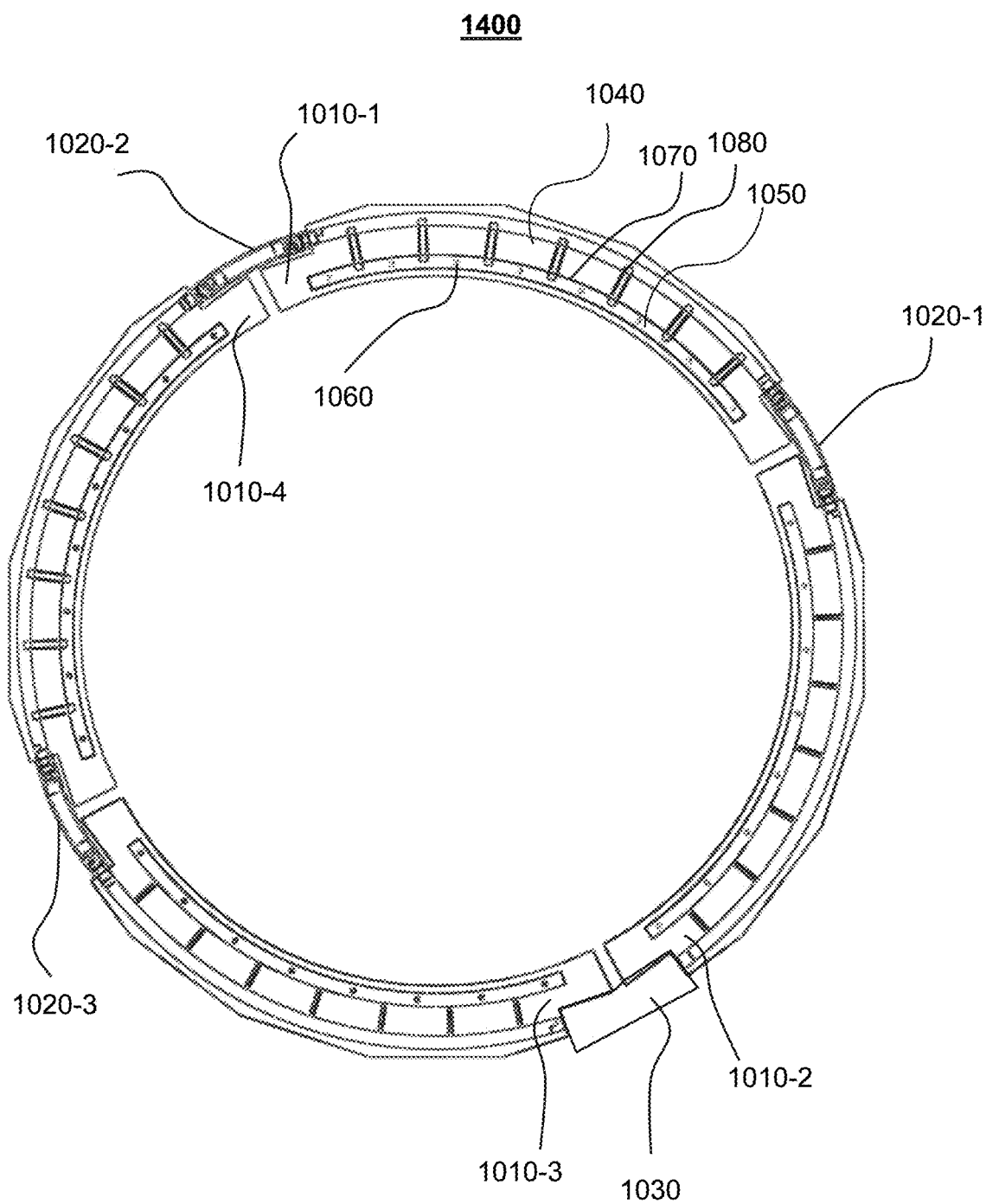
FIG. 15 is a perspective view of an exemplary separator according to some embodiments of the present disclosure.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the separator 710 may include at least one splitter plate (e.g., a first splitter 1070 and a second splitter 1080 as illustrated in FIG. 15) configured to separate the at least one separation chamber as described elsewhere in the present disclosure (e.g., FIG. 15 and descriptions thereof).

In some embodiments, the cooling assembly 700 may further include at least one sensor configured to detect a status of the cooling medium in the cooling assembly 700. The status of the cooling medium may include a temperature of the cooling medium, a flow rate of the cooling medium, a flow amount of the cooling medium, or the like, or any combination thereof. In some embodiments, the at least one sensor may be operably coupled to the separator 710, one or more of the plurality of delivering tubes, the collector 720, the cooling source, or the like, or any combination thereof. For example, the at least one sensor may be operably coupled to each delivering tube, and configured to detect the status of the cooling medium in the each delivering tube. As another example, the at least one sensor may be operably coupled to the cooling source, and configured to facilitate a control of the status of the cooling medium generated by the cooling source.

In some embodiments, the sensor may be connected to and/or communicate with one or more components (e.g., the storage device 130, the terminal 140, the processing device 120) of the imaging system 100. In some embodiments, the sensor may detect the status of the cooling medium in the cooling assembly 700 continuously or intermittently (e.g., periodically). The sensor may transmit the status of the cooling medium in the cooling assembly 700 to a control device (e.g., the terminal 140) for display and/or the processing device 120 periodically (e.g., every hour, every several hours, every day), e.g., if the status of the cooling medium in the cooling assembly 700 is determined to be within a normal range; or instantly, e.g., if the status of the cooling medium in the cooling assembly 700 is determined to be beyond the normal range (e.g., the temperature of the cooling medium is lower than a first temperature threshold, the temperature of the cooling medium is higher than a second temperature threshold, the flow rate of the cooling medium is lower than a first rate threshold, the flow rate of the cooling medium is higher than a second rate threshold). The terminal 140 or the processing device 120 may send a warning notification to a user (e.g., an operator) of the imaging system 100 if the status of the cooling medium in the cooling assembly 300 is determined to be beyond the normal range.

In some embodiments, the control device (e.g., the terminal 140, the processing device 120) may adjust the status of the cooling medium in the cooling assembly 700 based on an instruction provided by a user of the imaging system 100. In some embodiments, the control device (e.g., the terminal 140, the processing device 120) may adjust the status of the cooling medium in the cooling assembly 700 automatically. For example, the control device may control the status of the cooling medium in the separation main tube 711 by controlling the first switch or valve coupled to the separation main tube as described elsewhere in the present disclosure. As another example, the control device may control the status of the heat-laden cooling medium in the collection main tube 721 by controlling the second switch or valve coupled to the collection main tube as described elsewhere in the present disclosure. As still another example, the control device may control the status of the cooling medium generated by the cooling source by controlling one or more switches or valves coupled to the cooling source.

In some embodiments, the processing device 120 may perform a cooling simulation experiment on the cooling assembly 700. The sensor may detect the status of the cooling medium in the cooling assembly 700 in real time. The processing device 120 may improve the configuration of the cooling assembly 700 based on the real time status of the cooling medium in the cooling assembly 700 to achieve a desired cooling effect. For example, the processing device 120 may determine a number (or count) of levels of separation chambers, a number (or count) of splitter plates, or the like, in the cooling assembly 700 based on the real time status of the cooling medium in the cooling assembly 700.

Figure 10:
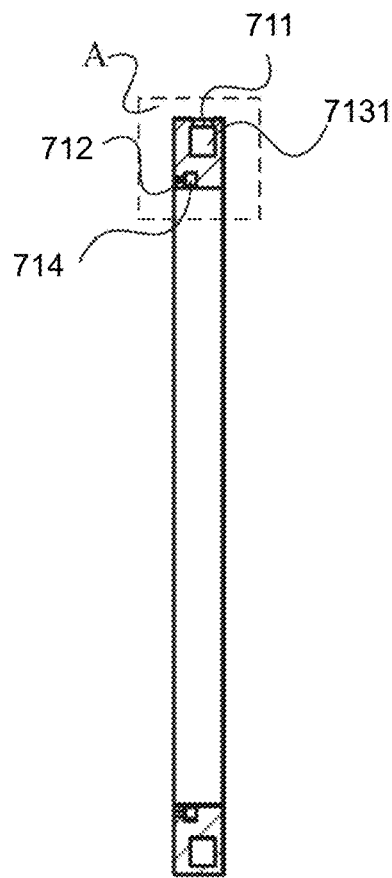
FIG. 10 is a sectional view along B-B' of FIG. 9 according to some embodiments of the present disclosure.
Figure 11:
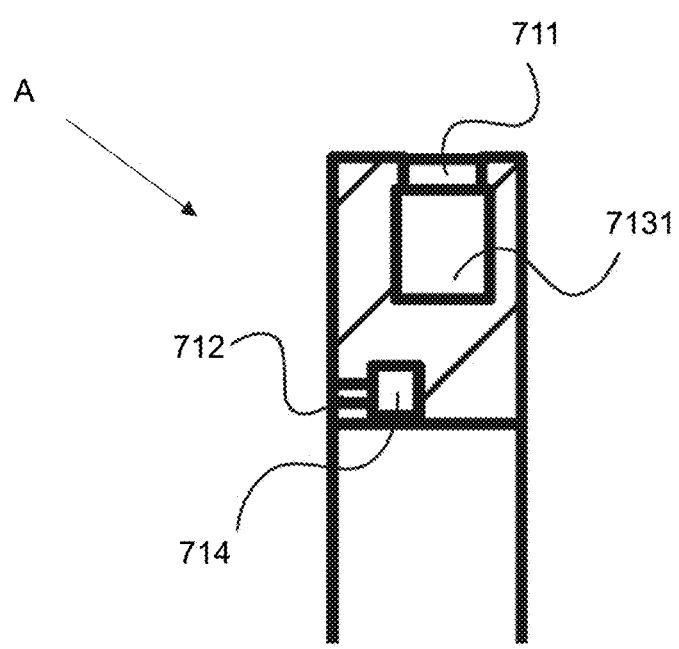
FIG. 11 is an enlarged view of the region A shown in FIG. 10 according to some embodiments of the present disclosure.
Figure 12:
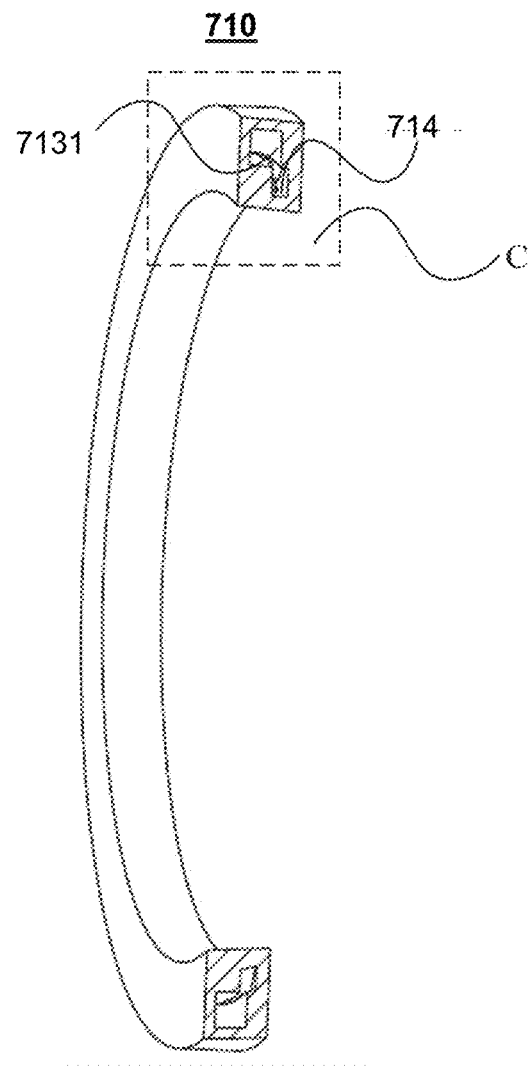
FIG. 12 illustrates an internal structure of the exemplary separator shown in FIG. 9 according to some embodiments of the present disclosure.
Figure 13:
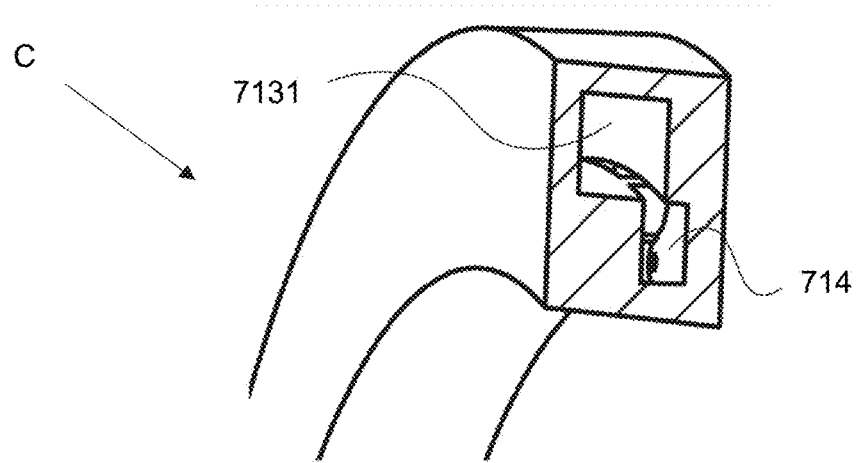
FIG. 13 is an enlarged view of the region C shown in FIG. 12 according to some embodiments of the present disclosure.

FIG. 9 is an axial sectional view of an exemplary separator according to some embodiments of the present disclosure. FIG. 10 is a sectional view along B-B' of FIG. 9 according to some embodiments of the present disclosure. FIG. 11 is an enlarged view of the region A shown in FIG. 10 according to some embodiments of the present disclosure. FIG. 12 illustrates an internal structure of the exemplary separator shown in FIG. 9 according to some embodiments of the present disclosure. FIG. 13 is an enlarged view of the region C shown in FIG. 12 according to some embodiments of the present disclosure.

As shown in FIG. 9, the separator 710 may include the separation main tube 711, a plurality of separation chambers 713, and the plurality of separation branch tubes 712. In FIG. 9, the plurality of separation chambers 713 may include two levels of separation chambers. For example, the plurality of separation chambers 713 may include a first-stage separation chambers 7131 and a plurality of last-stage separation chambers 7133. The first-stage separation chambers 7131 may be an annular separation chamber, as illustrated in FIGS. 9-13. The first-stage separation chamber 7131 may be in fluid communication with the plurality of last-stage separation chambers 7133. The separation main tube 711 may be in fluid communication with the first-stage separation chamber 7131. Each separation branch tube 712 may be in fluid communication with a last-stage separation chamber 7133.

In some embodiments, the plurality of last-stage separation chambers 7133 may include a plurality of separation grooves 714, as illustrated in FIGS. 9-13. The plurality of separation grooves 714 may be separated from each other. The first-stage separation chamber 7131 may be in fluid communication with the plurality of separation grooves 714. Each separation groove 714 of the plurality of separation grooves 714 may be in fluid communication with a corresponding separation branch tube 712 of the plurality of separation branch tubes 712.

In some embodiments, the separation groove 714 may have any suitable structure. For example, a cross section of a (e.g., each) separation groove 714 (in a plane perpendicular to the axial direction of the separator) may have a circle shape, a square shape, a rectangle shape, or an irregular shape, or the like. As another example, a cross section of a (e.g., each) separation groove 714 (in a plane perpendicular to the axial direction of the separator) may have a flat shape or a curved shape as illustrated in FIG. 9. The separation groove 714 with the cross section of curved shape or flat shape may facilitate the flow of the cooling medium from the separation groove 714 to the corresponding separation branch tube 712, which may ensure that the flow amount of the cooling medium in each separation groove 714 is uniform.

For illustration purposes, a cooling process is taken as an example. Specifically, a cooling medium may flow from a cooling source to the first-stage separation chamber 7131 via the separation main tube 711. The first-stage separation chamber 7131 may deliver a portion of the cooling medium into each last-stage separation chamber 7133 (e.g., each separation groove 714) of the plurality of last-stage separation chambers 7133 (e.g., the plurality of separation grooves 714), in response to an amount of the cooling medium in the first-stage separation chamber 7131 exceeding a threshold. The cooling medium may then flow from the each last-stage separation chamber 7133 (e.g., the each separation groove 714) of the plurality of last-stage separation chambers 7133 (e.g., the plurality of separation grooves 714) to each separation branch tube 712 of the plurality of separation branch tubes 712. The flow amount of the cooling medium in the each last-stage separation chamber 7133 may be uniform and sufficient to ensure that the cooling medium flows to each separation branch tube 712 of the plurality of separation branch tubes 712 uniformly. Accordingly, a circumferential flow gradient may be eliminated, and temperature gradient(s) among a plurality of detector modules may also be eliminated. The temperature of each detector module of the plurality of detector modules may be balanced (or substantially the same), which may ensure a consistent and stable response of the plurality of detector modules in the detector assembly. In addition, the imaging quality of the imaging device may be improved, which may facilitate diagnosis of the scanned object.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 14:
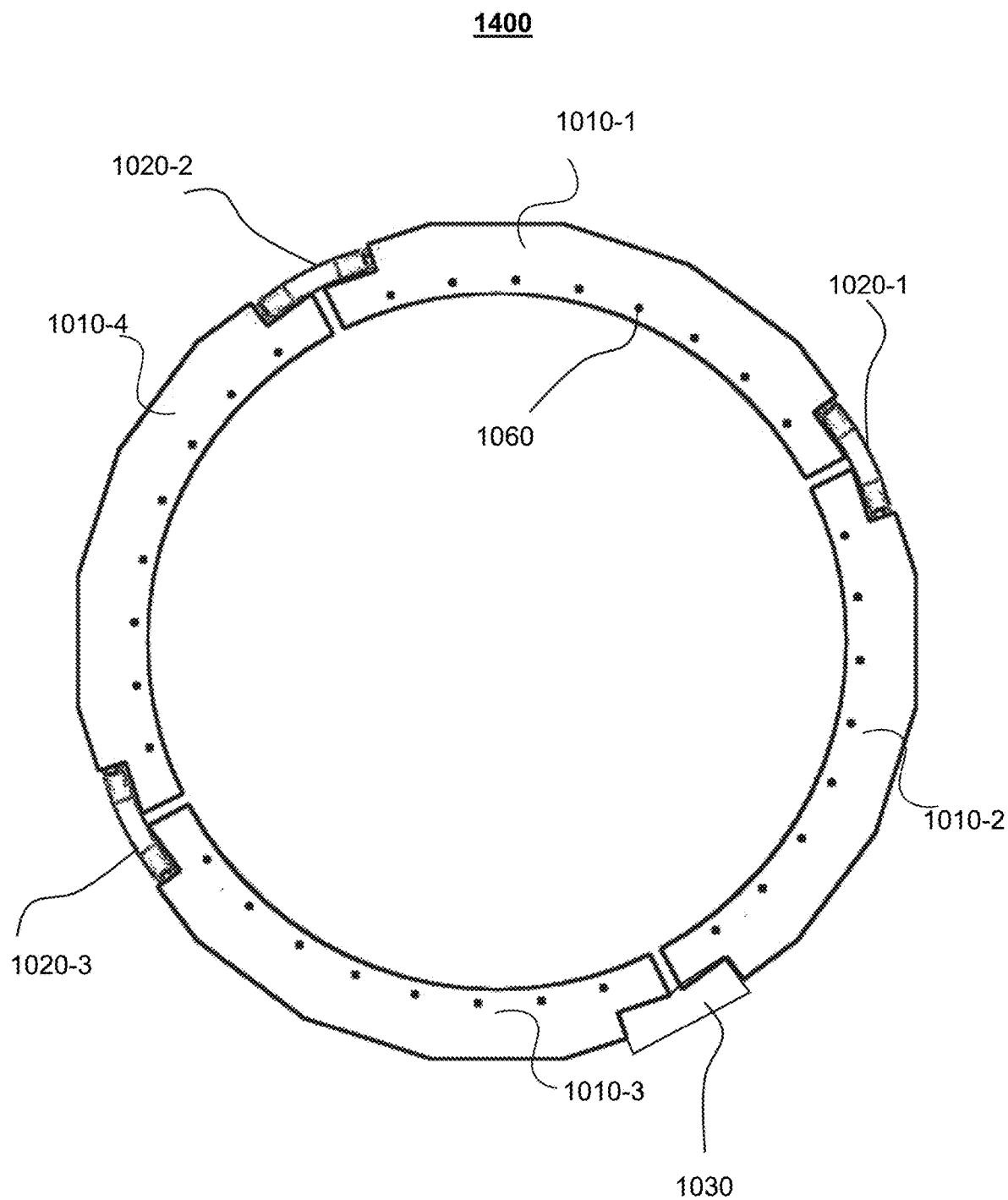
FIG. 14 is a schematic diagram illustrating an exemplary separator according to some embodiments of the present disclosure.

FIG. 14 is a schematic diagram illustrating an exemplary separator according to some embodiments of the present disclosure. FIG. 15 is a perspective view of an exemplary separator according to some embodiments of the present disclosure. In some embodiments, a separator 1400 may be an example of the separator 710 or a portion of the separator 710.

As illustrated in FIGS. 14 and 15, the separator 1400 may include a plurality of sub-separators (e.g., a sub-separator 1010-1, a sub-separator 1010-2, a sub-separator 1010-3, and a sub-separator 1010-4). Each of the plurality of sub-separators may have an arc shape. The plurality of sub-separators may be connected with each other to form the separator 1400. In some embodiments, the separator 1400 may have an enclosed structure. The separator 1400 may be configured as a complete circle. The plurality of sub-separators may be in fluid communication with each other. For example, each sub-separator may be in fluid communication with one or more adjacent sub-separators. In some embodiments, adjacent sub-separators of the plurality of sub-separators may be connected with each other via a connection tube (e.g., a connection tube 1020-1, a connection tube 1020-2, and a connection tube 1020-3). The connection tube configured between two adjacent sub-separators may be in fluid communication with each of the two adjacent sub-separators.

According to some embodiments of the present disclosure, the separator 1400 may be assembled using the plurality of sub-separators. In some embodiments, compared with the weight of the separator 1400, the weight of a sub-separator is relatively small and a volume of the sub-separator is relatively small, which may facilitate the transportation and/or the assembly of the separator 1400. In addition, a manufacturing process of the sub-separator may be relatively simple. The accuracy of the manufacturing process may also be improved.

In some embodiments, the separator 1400 may include at least one separation main tube (e.g., the separation main tube 1030). The at least one separation main tube (e.g., the separation main tube 1030) may be in fluid communication with at least one sub-separator of the plurality of sub-separators. For example, the at least one separation main tube may be configured on or coupled to the at least one sub-separator of the plurality of sub-separators. As another example, the at least one separation main tube (e.g., the separation main tube 1030) may be configured on or coupled to at least one connection between two adjacent sub-separators of the plurality of sub-separators. In some embodiments, a number (or count) of the separation main tubes may be determined based on a number (or count) of sub-separators according to one or more iterative experiments, to achieve a desired cooling effect.

As illustrated in FIGS. 14 and 15, the sub-separator 1010-1 may be in fluid communication with the sub-separator 1010-2 via the connection tube 1020-1. The sub-separator 1010-1 may be in fluid communication with the sub-separator 1010-4 via the connection tube 1020-2. The sub-separator 1010-4 may be in fluid communication with the sub-separator 1010-3 via the connection tube 1020-3. The separation main tube 1030 may be configured on a connection between the sub-separator 1010-2 and the sub-separator 1010-3. The separation main tube 1030 may be in fluid communication with the sub-separator 1010-2 and the sub-separator 1010-3. For illustration purposes, a cooling medium may flow from a cooling source to the sub-separator 1010-2 and the sub-separator 1010-3 via the separation main tube 1030. The cooling medium may then flow from the sub-separator 1010-2 and the sub-separator 1010-3 to the sub-separator 1010-1 and the sub-separator 1010-4 via the connection tube 1020-3 and the connection tube 1020-1, respectively. Accordingly, the cooling medium may be distributed in the plurality of sub-separators of the separator 1400.

In some embodiments, each sub-separator may include at least one separation chamber (e.g., a first-stage separation chamber 1040, a last-stage separation chambers 1050) and a plurality of separation branch tubes 1060. In some embodiments, the at least one separation chamber may include at least two levels of separation chambers as described elsewhere in the present disclosure. For example, as illustrated in FIG. 15, the at least one separation chamber of a sub-separator may include a plurality of first-stage separation chambers 1040 and a plurality of last-stage separation chambers 1050. Each of the plurality of first-stage separation chambers 1040 may be in fluid communication with at least one last-stage separation chamber 1050 of the plurality of last-stage separation chambers 1050. The separation main tube 1030 may be in fluid communication with the plurality of first-stage separation chambers 1040 of the plurality of sub-separators. The each separation branch tube 1060 may be in fluid communication with a last-stage separation chamber 1050.

In some embodiments, a width of the connection tube and/or a height of the first-stage separation chamber 1040 may be less than a threshold. As used herein, "a width of a connection tube (or a height of a first-stage separation chamber)" may refer to its length between an outer surface of the connection tube (or the first-stage separation chamber) and an inner surface of the connection tube (or the first-stage separation chamber). An inner surface of the connection tube (or the first-stage separation chamber) may refer to a surface that is close to or faces a scanned object and an outer surface of the connection tube (or the first-stage separation chamber) may refer to a surface that is away from or opposite to the scanned object. Therefore, after the cooling medium flows from the cooling source to the plurality of first-stage separation chambers 1040 through the separation main tube 1030, the cooling medium may quickly flow into the plurality of first-stage separation chambers 1040 of the separator 1400, which may achieve a uniform flow of the cooling medium in the separator 1400.

In some embodiments, the separator 1400 may include at least one splitter plate (e.g., a first splitter 1070, a second splitter 1080) configured to separate the at least one separation chamber. In some embodiments, the separator 1400 may include at least one first splitter plate (e.g., the first splitter 1070) configured to separate the at least two levels of separation chambers. Each of the at least one first splitter plate (e.g., the first splitter 1070) may include a connection area (not shown in FIG. 15) configured to allow a fluid communication between adjacent separation chambers of different levels of separation chambers. For example, an upper-stage separation chamber (e.g., the first-stage separation chamber 1040) and a lower-stage separation chamber (e.g., the last-stage separation chambers 1050) may be separated by the first splitter plate 1070 such that the upper-stage separation chamber (e.g., the first-stage separation chamber 1040) and the lower-stage separation chamber (e.g., the last-stage separation chambers 1050) are not in fluid communication with each other except through the connection area formed on the first splitter plate 1070. In some embodiments, the separator 1400 may include at least one second splitter plate (e.g., the second splitter plate 1080) configured to separate the at least one separation chamber in a same level of separation chambers. Each of the at least one second splitter (e.g., the second splitter plate 1080) may include a connection area (not shown in FIG. 15) configured to allow a fluid communication between adjacent separation chambers of the same level of separation chambers. For example, adjacent first-stage separation chambers 1040 may be separated by the second splitter plate 1080 such that the adjacent first-stage separation chambers 1040 are not in fluid communication with each other except through the connection area formed on the second splitter plate 1080.

In some embodiments, the plurality of separation chambers (e.g., the first-stage separation chamber 1040, the last-stage separation chambers 1050) may be separated by the plurality of splitter plates (e.g., the first splitter 1070, the second splitter 1080), such that the plurality of separation chambers are not in fluid communication with each other except through connection areas formed on the plurality of splitter plates. This configuration may ensure that the cooling medium can flow from an upper-stage separation chamber (e.g., the first-stage separation chamber 1040) to a lower-stage chamber (e.g., the last-stage separation chambers 1050) uniformly. For example, if a separator (e.g., the separator 1400) includes two levels of separation chambers, the cooling medium may flow from the plurality of first-stage separation chambers 1040 to the plurality of last-stage separation chambers 1050 uniformly. As another example, if a separator includes three or more levels of separation chambers, the cooling medium may flow from a plurality of first-stage separation chambers to a plurality of intermediate-stage separation chambers (e.g., a plurality of second-stage separation chambers, a plurality of third-stage separation chambers) uniformly. The cooling medium may then flow from the plurality of intermediate-stage separation chambers to the plurality of last-stage separation chambers uniformly. Therefore, the flow amount of the cooling medium in each separation branch tube may be uniform.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, a structure of a collector may be the same as or similar to a structure of the separator 1400, and detailed descriptions of the collector may not be repeated here.

FIGS. 16 and 17 are schematic diagrams illustrating an exemplary separator according to some embodiments of the present disclosure. As illustrated in FIG. 16, a separator 1600 may include a separation main tube (not shown in FIGS. 16 and 17), a separation chamber 1610, and a plurality of separation branch tubes 1620. The separation chamber 1610 may be an annular separation chamber. The separation main tube may be in fluid communication with the separation chamber 1610. The plurality of separation branch tubes 1620 may be in fluid communication with the separation chamber 1610. As illustrated in FIG. 17, a plurality of separation outlets 1640 may be configured on the separator 1600. The plurality of separation branch tubes 1620 may be mounted on or coupled to the separator 1600 via the plurality of separation outlets 1640. A number (or count) of the separation outlets 1640 may be the same as a number (or count) of separation branch tubes 1620. For example, the number (or count) of the separation outlets 1640 and the number (or count) of separation branch tubes 1620 may be 32, as illustrated in FIG. 16.

For illustration purposes, a cooling medium may flow from a cooling source to the separation chamber 1610 via the separation main tube. The cooling medium may then flow from the separation chamber 1610 to the plurality of separation branch tubes 1620. A portion of the cooling medium may flow from each of the plurality of separation branch tubes 1620 to one of a plurality of delivering tubes to absorb heat from a target portion (e.g., a detector module) of an imaging device. In some embodiments, a collector may have a same or similar structure as illustrated in FIGS. 16 and 17.

Figure 18:
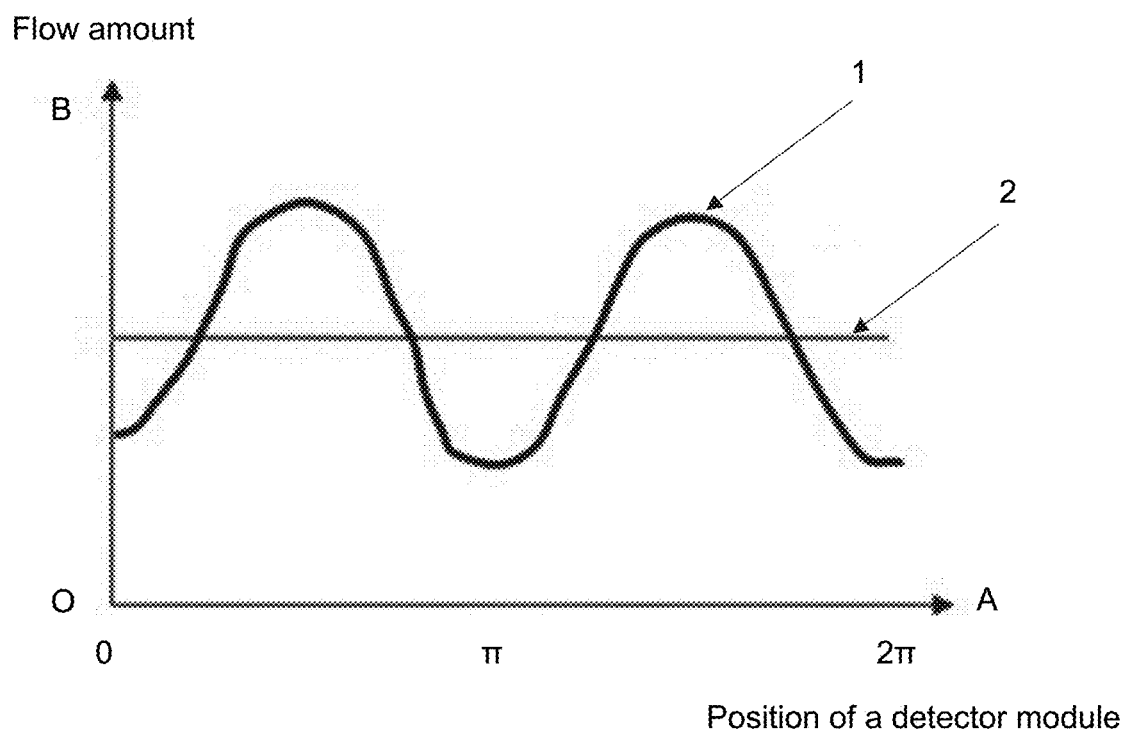
FIG. 18 is a schematic diagram illustrating a relationship between a flow amount of a cooling medium and a position of a detector module according to some embodiments of the present disclosure.

FIG. 18 is a schematic diagram illustrating a relationship between a flow amount of a cooling medium and a position of a detector module according to some embodiments of the present disclosure.

As shown in FIG. 18, an axis OB corresponds to a flow amount of a cooling medium, and an axis OA corresponds to a position of a detector module in a detector assembly. In some embodiments, a plurality of detector modules may be arranged on an inner surface of a supporting component (e.g., the supporting component 750) circumferentially to form a plurality of detector rings along an axial direction of a cooling assembly (e.g., the cooling assembly 700). The position of the detector module may be represented as a radian with $0\sim2\pi$ along a circumferential direction of the detector ring, as shown in FIGS. 16 and 18. In FIG. 18, curve 1 refers to an actual relationship between the flow amount of the cooling medium and the position of the detector module. Curve 2 refers to an ideal relationship between the flow amount of the cooling medium and the position of the detector module. As shown in FIGS. 16 and 18, by using the separator 1600, the flow amounts of the cooling medium at different positions of the detector module may be different. If the position of the detector module changes from 0 to $\pi$, the flow amount of the cooling medium may increase and then decrease. At a position of $\pi/2$, the flow amount of the cooling medium may reach a highest value. If the position of the detector module changes from $\pi$ to $2\pi$, the flow amount of the cooling medium may increase and then decrease. At a position of $\pi 3/2$, the flow amount of the cooling medium may reach the highest value. In an ideal situation, as shown in curve 2, the flow amounts of the cooling medium of the detector modules at different positions may be the same.

FIGS. 19 and 20 are schematic diagrams illustrating an exemplary separator according to some embodiments of the present disclosure. A separator 1900 may be similar to the separator 1600, except for certain components or features. As illustrated in FIGS. 19 and 20, the separator 1900 may include a separation main tube (not shown in FIGS. 19 and 20), a plurality of separation chambers 1910, a plurality of separation branch tubes 1920, a plurality of separation outlets 1940, and a plurality of splitter plates 1930. Each separation chamber 1910 of the plurality of separation chambers 1910 may be in fluid communication with a separation branch tube 1920 of the plurality of separation branch tubes 1920.

The splitter plate 1930 may be configured to separate the plurality of separation chambers 1910. Each of the plurality of splitter plates 1930 may include a connection area configured to allow a fluid communication between adjacent separation chambers 1910 of the plurality of separation chambers 1910. In some embodiments, the splitter plate 1930 may increase a resistance and reduce a flow rate and/or a flow amount of the cooling medium at the corresponding separation outlet 1940, which may ensure a uniform distribution of the cooling medium in the plurality of separation chambers 1910. Accordingly, the flow amount of the cooling medium in each separation branch tube 1920 of the plurality of separation branch tubes 1920 may be relatively uniform.

FIGS. 21 and 22 are schematic diagrams illustrating an exemplary separator according to some embodiments of the present disclosure. A separator 2100 may be similar to the separator 1900, except for certain components or features. As illustrated in FIGS. 21 and 22, the separator 2100 may include a separation main tube (not shown in FIGS. 21 and 22), a plurality of separation chambers 2110, a plurality of separation branch tubes 2120, a plurality of separation outlets 2140, and a plurality of splitter plates 2130. Each separation chamber 2110 of the plurality of separation chambers 2110 may be in fluid communication with one or more separation branch tube 2120 of the plurality of separation branch tubes 2120. Because the flow amount of the cooling medium of the detector modules at a position of $\pi/2$ and a position of $3\pi/2$ are highest (as illustrated in FIG. 18), the splitter plate 2130 may be mounted on or configured at the position of $\pi/2$ and the position of $3\pi/2$ to reduce the flow amount of the cooling medium of the detector modules at the separation outlets 2140 corresponding to the position of $\pi/2$ and the position of $3\pi/2$, such that the flow amount of the cooling medium flowing out from each separation outlet 2140 is relatively uniform.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

We claim:

1. A detector module for a device, comprising:
a crystal array including a plurality of crystal units; and
a shielding component configured to house the crystal array, wherein the shielding component includes:
a cover including an accommodating region configured to accommodate the crystal array; and
a connection component configured to connect the detector module to the device, the connection component being operably coupled to the crystal array and the cover,
wherein the cover further includes a plurality of boards, each board of the plurality of boards includes a base layer and a shielding layer Placed on an outer surface of the base layer, the shielding layer is in contact with the connection component, and the shielding layer is configured to conduct an electrical current with the connection component.

2. The detector module of claim 1, wherein the shielding component further includes a Faraday cage.

3. The detector module of claim 2, wherein the Faraday cage is coupled to or integrated in the cover of the shielding component.

4. The detector module of claim 1, wherein at least one of the plurality of boards is detachable.

5. The detector module of claim 4, wherein the plurality of boards includes a first board and a second board, and at least one of the first board or the second board has a U-shaped cross section.

6. The detector module of claim 5, wherein at least one side of the first board is bent toward the crystal array or bent away from the crystal array to form a protruding part, and a corresponding side of the second board is abutted against the protruding part.

7. The detector module of claim 1, wherein shielding layers of adjacent boards in the plurality of boards are in contact with each other.

8. The detector module of claim 1, wherein an inner surface of the base layer includes a plurality of convex portions, and the connection component includes a plurality of concave portions corresponding to the plurality of convex portions.

9. The detector module of claim 1, wherein an inner surface of the base layer includes a plurality of concave portions, and the connection component includes a plurality of convex portions corresponding to the plurality of concave portions.

10. A cooling assembly for a device, comprising:
a separator including a separation main tube, at least one separation chamber, and a plurality of separation branch tubes, wherein the separation main tube is in fluid communication with the at least one separation chamber, and the plurality of separation branch tubes are in fluid communication with the at least one separation chamber, the at least one separation chamber includes one or more first-stage separation chambers and one or more last-stage separation chambers, each of the one or more first-stage separation chamber is an annular separation chamber, the one or more last-stage separation chambers include a plurality of separation grooves, the plurality of separation grooves are arranged along a circumferential direction of the at least one first-stage separation chamber, and each of the one or more first-stage separation chambers is in fluid communication with two or more of the plurality of separation grooves;

a plurality of delivering tubes configured to deliver a cooling medium, wherein each delivering tube of the plurality of delivering tubes is in fluid communication with each separation branch tube of the plurality of separation branch tubes, the each delivering tube correspond to a detector module of the device, and the each delivering tube is configured to deliver a portion of the cooling medium to the corresponding detector module of the device; and a collector including a collection main tube and a plurality of collection branch tubes, wherein each collection branch tube of the plurality of collection branch tubes is in fluid communication with the each delivering tube of the plurality of delivering tubes.

11. The cooling assembly of claim 10, wherein
the separation main tube is in fluid communication with the one or more first-stage separation chambers, and
the each separation branch tube is in fluid communication with one of the one or more last-stage separation chambers.

12. The cooling assembly of claim 10, wherein an upper-stage separation chamber of the at least one separation chamber is configured to deliver a portion of the cooling medium into a lower-stage separation chamber of the at least one separation chamber, in response to an amount of the cooling medium in the upper-stage separation chamber exceeding a threshold.

13. The cooling assembly of claim 10, wherein each separation groove of the plurality of separation grooves is in fluid communication with at least one separation branch tube of the plurality of separation branch tubes.

14. The cooling assembly of claim 10, wherein a cross section of the each separation groove of the plurality of separation grooves has a curved shape or a flat shape.

15. The cooling assembly of claim 10, wherein
the at least one separation chamber includes one or more intermediate-stage separation chambers between the one or more first-stage separation chambers and the one or more last-stage separation chambers, and
one of the one or more intermediate-stage separation chambers is in fluid communication with at least one of the one or more first-stage separation chambers and at least one of the one or more last-stage separation chambers.

16. The cooling assembly of claim 10, wherein
the separator includes at least one splitter plate configured to separate the at least one separation chamber, and
each of the at least one splitter plate includes a connection area configured to allow a fluid communication between adjacent separation chambers of the at least one separation chamber.

17. A system, comprising:
a gantry;
a detector assembly including a plurality of detector modules arranged on the gantry; and
a cooling assembly configured to cool the detector assembly,
wherein
each of the plurality of detector modules includes a crystal array configured to detect radiation rays, and a shielding component configured to shield the crystal array from an electromagnetic interference, wherein the shielding component includes a cover including an accommodating region configured to accommodate the crystal array and a connection component configured to connect the detector module to the gantry, the connection component is operably coupled to the crystal array and the cover; and
the cooling assembly includes a plurality of cooling components, each of the plurality of cooling components being embedded in a corresponding detector module of the plurality of detector modules;
the cover further includes a plurality of boards, each board of the plurality of boards includes a base layer and a shielding layer Placed on an outer surface of the base layer, the shielding layer is in contact with the connection component, and the shielding layer is configured to conduct an electrical current with the connection component.

* * * * *